(12) United States Patent
Toranto et al.

(10) Patent No.: US 8,067,188 B2
(45) Date of Patent: *Nov. 29, 2011

(54) ANALYTE DETECTION

(75) Inventors: Anthony Toranto, San Diego, CA (US); Evan Singer, Ross, CA (US); Brett Miller, Atherton, CA (US)

(73) Assignee: N2ITIVE1 Innovations, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/761,530

(22) Filed: Apr. 16, 2010

(65) Prior Publication Data

US 2010/0255497 A1 Oct. 7, 2010

Related U.S. Application Data

(63) Continuation of application No. 09/976,872, filed on Oct. 12, 2001, now Pat. No. 7,700,305, which is a continuation-in-part of application No. 09/968,306, filed on Oct. 27, 2000, now Pat. No. 6,730,494, and a continuation-in-part of application No. 09/398,552, filed on Sep. 17, 1999, now abandoned.

(60) Provisional application No. 60/243,854, filed on Oct. 27, 2000.

(51) Int. Cl.
*G01N 31/00* (2006.01)
*G01N 33/53* (2006.01)

(52) U.S. Cl. .......... 435/7.21; 435/7.1; 435/28; 436/132; 436/501; 436/518; 424/9.1; 424/520

(58) Field of Classification Search .................. None
See application file for complete search history.

(56) References Cited

U.S. PATENT DOCUMENTS

| | | | |
|---|---|---|---|
| 2,853,206 A | 9/1958 | Uxa | |
| 3,410,455 A | 11/1968 | Haas | |
| 3,565,284 A | 2/1971 | Hinterreiter | |
| 3,802,842 A | 4/1974 | Lange | |
| 3,844,445 A | 10/1974 | Haas | |
| 3,845,882 A | 11/1974 | Hass | |
| 3,875,013 A | 4/1975 | Manautou | |
| 3,915,639 A | 10/1975 | Friedenberg | |
| 3,942,683 A | 3/1976 | Haas | 221/229 |
| 4,110,079 A | 8/1978 | Schaeffer et al. | 422/56 |
| 4,171,753 A | 10/1979 | Vreede | 221/197 |
| 4,361,648 A | 11/1982 | Shuenn-tzong | 435/20 |
| 4,430,427 A | 2/1984 | Hopkins | 435/25 |
| 4,440,724 A | 4/1984 | Tabb et al. | |
| 4,444,880 A | 4/1984 | Tom | |
| 4,562,043 A | 12/1985 | Mennen | |
| 4,629,697 A | 12/1986 | Limbach et al. | 435/26 |
| 4,642,286 A | 2/1987 | Moldowan | 435/25 |
| 4,677,059 A | 6/1987 | Beutler et al. | 435/25 |
| 4,729,956 A | 3/1988 | Hopkins | 435/188 |
| 4,734,360 A | 3/1988 | Phillips | 435/25 |
| 4,786,596 A | 11/1988 | Adams | 435/28 |
| 4,810,633 A | 3/1989 | Bauer et al. | 435/25 |
| 4,853,325 A | 8/1989 | Vodian | |
| 4,900,666 A | 2/1990 | Phillips | 435/25 |
| 4,911,344 A | 3/1990 | Kahler | 221/135 |
| 4,962,025 A | 10/1990 | Moldowan | 435/25 |
| 4,978,612 A | 12/1990 | Kobayashi et al. | 435/10 |
| 4,999,287 A | 3/1991 | Allen et al. | 435/11 |
| 5,032,506 A | 7/1991 | Palmer et al. | 435/26 |
| 5,081,015 A | 1/1992 | Hayashi et al. | 435/14 |
| 5,091,153 A | 2/1992 | Bachand | 422/58 |
| 5,116,729 A | 5/1992 | Ismail et al. | 435/14 |
| 5,126,247 A | 6/1992 | Palmer et al. | 435/4.25 |
| 5,141,854 A | 8/1992 | Kaufman et al. | 435/26 |
| 5,173,433 A | 12/1992 | Bachand | 436/169 |
| 5,190,872 A | 3/1993 | Hashizume et al. | 435/176 |
| 5,290,683 A | 3/1994 | Israel et al. | 435/26 |
| 5,334,502 A * | 8/1994 | Sangha | 435/7.21 |
| 5,366,902 A | 11/1994 | Cox et al. | 435/165 |
| 5,376,337 A | 12/1994 | Seymour | |
| 5,384,264 A | 1/1995 | Chen et al. | 436/164 |
| 5,403,749 A | 4/1995 | Khartchenko et al. | 436/132 |
| 5,416,004 A | 5/1995 | Detwiler | 435/26 |
| 5,429,931 A | 7/1995 | Detwiler et al. | 435/26 |
| 5,429,932 A | 7/1995 | Detwiler et al. | 435/26 |
| 5,494,831 A | 2/1996 | Kindler | |
| 5,500,351 A | 3/1996 | Eccles et al. | 435/25 |
| 5,500,375 A | 3/1996 | Lee-Own et al. | 436/514 |
| 5,500,506 A | 3/1996 | Lawson | 219/121.67 |
| 5,505,308 A | 4/1996 | Eikmeier et al. | |
| 5,525,481 A | 6/1996 | Kaufman et al. | 435/26 |

(Continued)

FOREIGN PATENT DOCUMENTS

EP 0019937 12/1980

(Continued)

OTHER PUBLICATIONS

Levitskii et al. (Ukrainskii Biokimicheskii Zhurnal, 1979, vol. 51, No. 3, pp. 289-292, English Abstract Only).*
AlcoScreen; excertp taken from http://craigmedical.com and http://chematics.com.
Gronow, Trends Biochem. Sci. 9: 336 [984].
Brinker and Scherer, Sol-Gel Science, Academic Press, San Diego [1995].
Avnir, Accounts Chem. Res. 28: 328 [1995].
Yamanaka et al., Am. Chem. Soc. 117: 9095 [1995].
Miller et al., Non-Cryst. Solids 202: 279 [1996].
Dave et al., Anal. Chem. 66: 1120A [1994.
Penttila et al., "Alcohol Screening with the Alcoscan test strip in forensic praxis," *Forensic Sci Int* 44(a):43-8 (1990) (Abstract only).
Harpe et a., "Saliva alcohol reagent strips in altered response protocols," *Prehospital Disasster Med* 5(1)41-3 discussion 43-4 (1990) (Abstract only).
Hansen et a.., "Measurement of alcohol in saliva with a test strip," *Ugeskr Laeger* 151(5):300-2 (1989) (Abstract only).
Arola, "The strip test for hypolactasia also works without ethanol," *Scand J Gastroenterol* 23(7):851-5 (1988) (Abstract only).

(Continued)

*Primary Examiner* — Lisa Cook

(74) *Attorney, Agent, or Firm* — Casimir Jones, S.C.

(57) ABSTRACT

The present invention relates to analyte detection test systems, including test systems for the oral detection of analytes in saliva. The present invention also provides compositions and methods for storing multiple assay tests and compositions and methods for measuring the concentration of analytes in a sample.

5 Claims, 15 Drawing Sheets

U.S. PATENT DOCUMENTS

| | | | |
|---|---|---|---|
| 5,527,509 A | 6/1996 | Gibson et al. | 422/56 |
| 5,563,031 A | 10/1996 | Yu | 435/4 |
| 5,563,073 A * | 10/1996 | Titmas | 436/132 |
| 5,571,395 A | 11/1996 | Park et al. | 204/403 |
| 5,585,273 A | 12/1996 | Lawrence et al. | 435/288.7 |
| 5,589,349 A | 12/1996 | Shinzaki et al. | 435/26 |
| 5,643,721 A | 7/1997 | Spring et al. | |
| 5,656,502 A | 8/1997 | MacKay et al. | 436/180 |
| 5,714,341 A | 2/1998 | Thieme et al. | |
| 5,720,924 A | 2/1998 | Eikmeier | |
| 5,788,064 A | 8/1998 | Sacherer et al. | |
| 5,792,621 A | 8/1998 | Verostko et al. | 435/14 |
| 5,795,543 A | 8/1998 | Poto et al. | 436/95 |
| 5,800,779 A | 9/1998 | Johnson | 422/58 |
| 5,911,937 A | 6/1999 | Hekal | 264/255 |
| 5,962,333 A | 10/1999 | Incorvia | |
| 6,080,350 A | 6/2000 | Hekal | 264/255 |
| 6,102,872 A | 8/2000 | Doneen | |
| 6,162,397 A | 12/2000 | Jurik | |
| 6,194,224 B1 | 2/2001 | Good | |
| 6,248,598 B1 | 6/2001 | Bogema | |
| 6,378,702 B1 | 4/2002 | Kintzig | |
| 6,670,192 B1 | 12/2003 | Galen | |

FOREIGN PATENT DOCUMENTS

| | | | |
|---|---|---|---|
| JP | 2109998 A | 4/1990 | |
| JP | 2176565 A | 7/1990 | |
| JP | 88 263265 A | 2/1998 | |
| JP | 88 330851 A | 5/1998 | |
| WO | WO 98/39231 | 9/1998 | |
| WO | WO 99/62697 | 12/1999 | |
| WO | WO 99/63288 | 12/1999 | |
| WO | WO 00/17259 | 3/2000 | |
| WO | WO 0017636 | 3/2002 | |

OTHER PUBLICATIONS van Keulen et al., "The LysR-type transcriptional regulator CbbR controlling autotrophic CO2 fixation by Xanthobacter flavus in an NADPH sensor," *J. Bacteriol* 180(6):1411-7 (1988)—PubMed medline query (Abstract only).

Onsiote Alcohol—Assay for the Qualitative Detection of Alcohol in Urine and Saliva, Rapid Diagnostics/Point of Care, On-Site (Brochure).

Alcohol And Quantitative Alcohol Tests Using Saliva, http://www.gdi,net/fohg/alcohol.htm (Advertisement).

ALCO Screen 02, 4-Minute Saliva Test by Blood Alcohol (Brochure).

Home Health Testing, BreachScan—A Breath Alcohol Detector, wysiwyg://25/http://www.alcoholtesting.com.

Home Health Testing, Saliva Drug Tests, http://www.alcoholtesting.com/salivadrugtests.htm.

\* cited by examiner

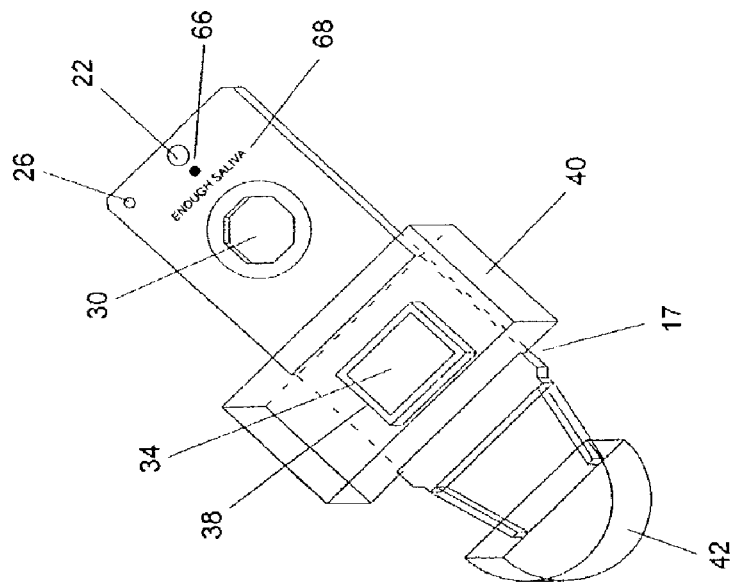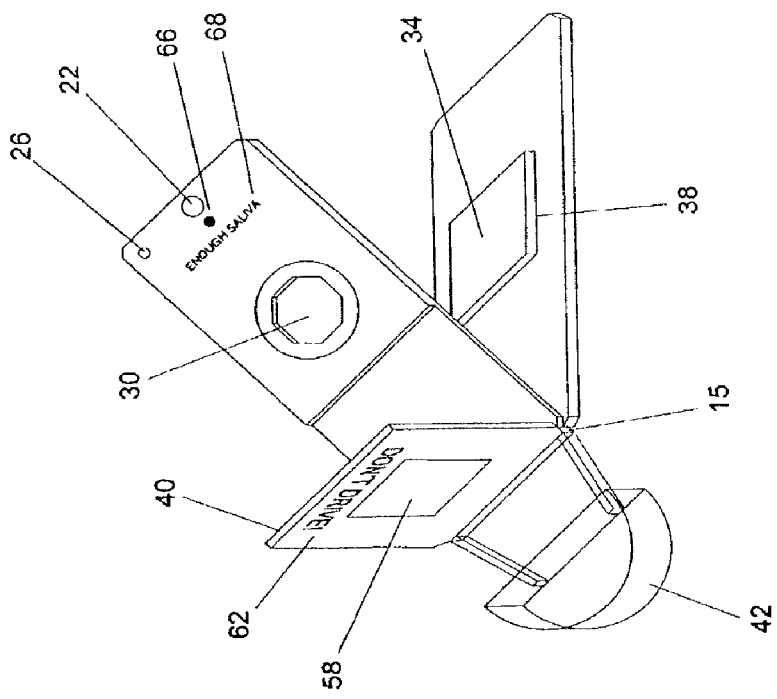

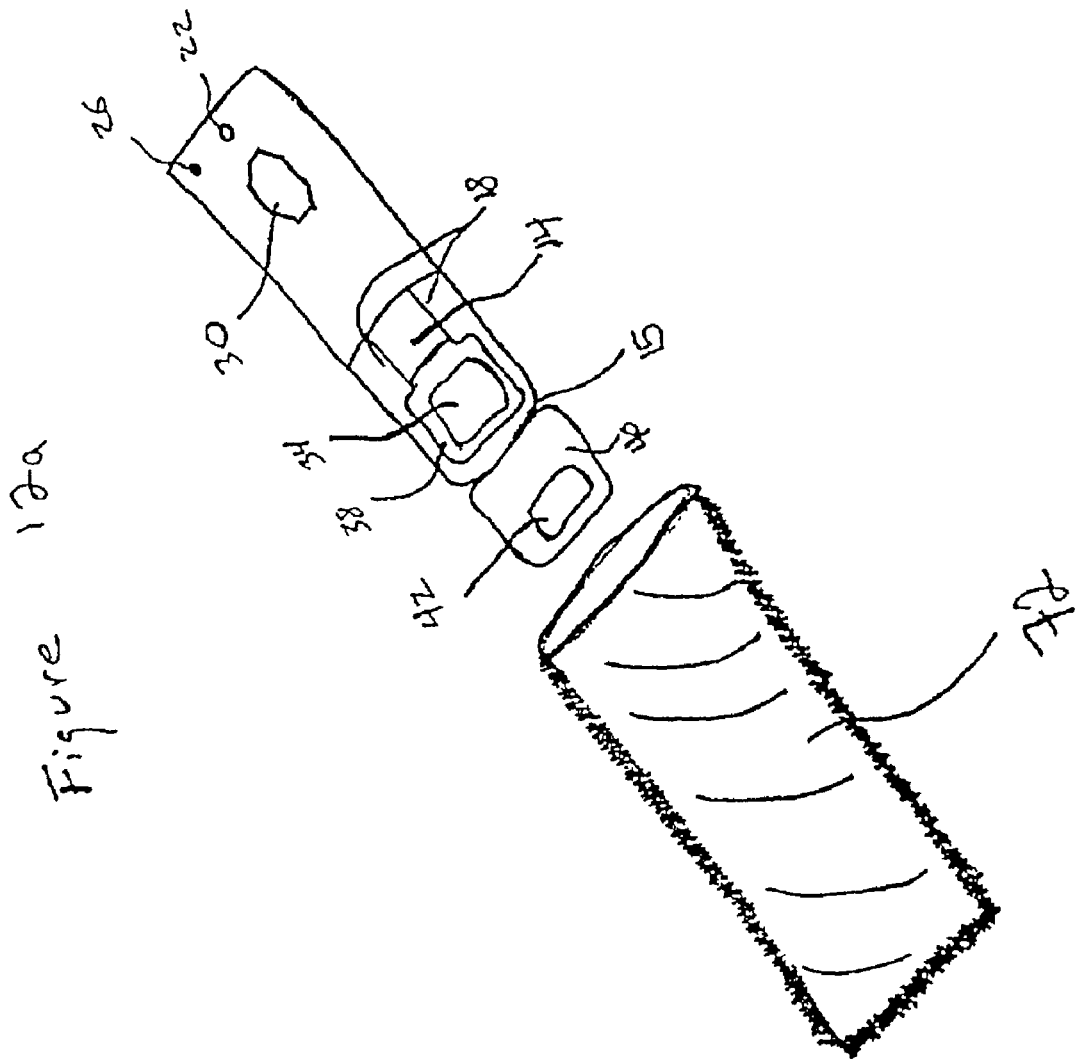

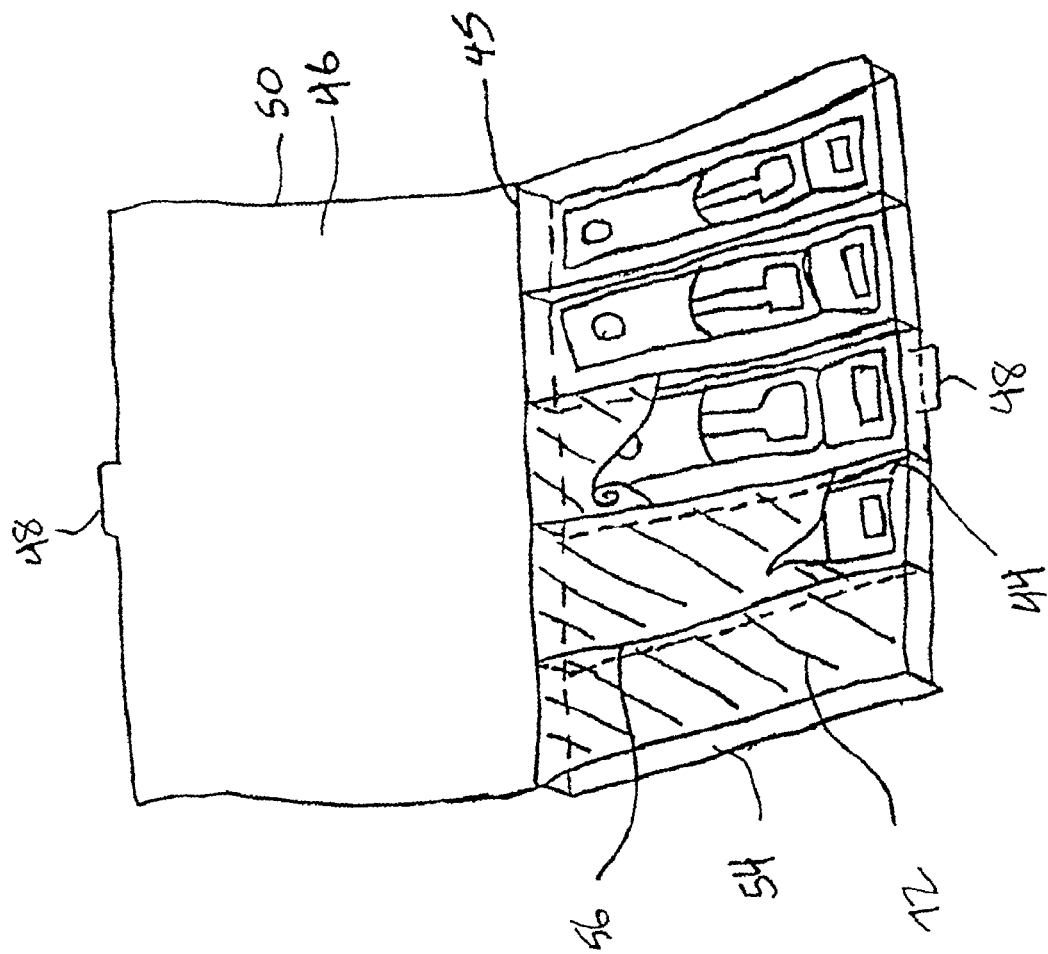

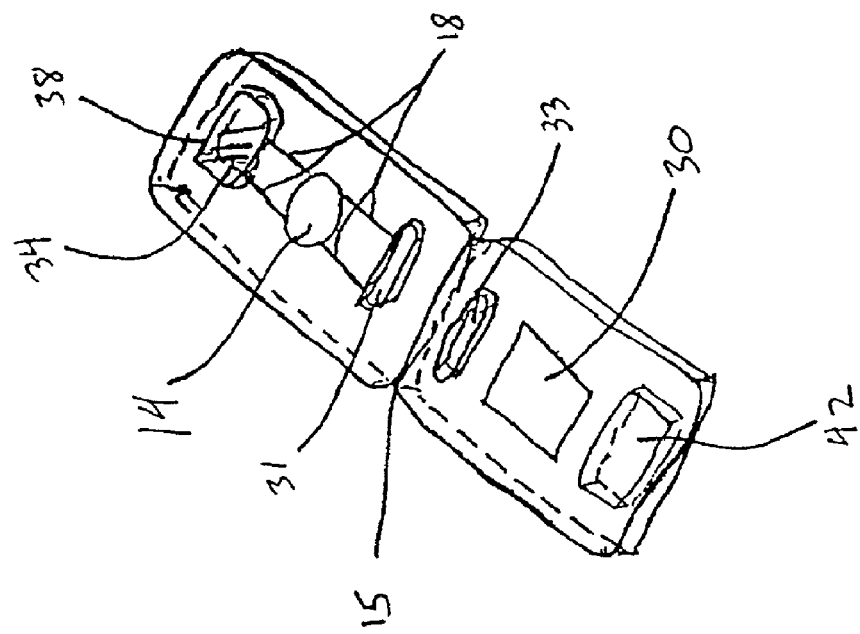
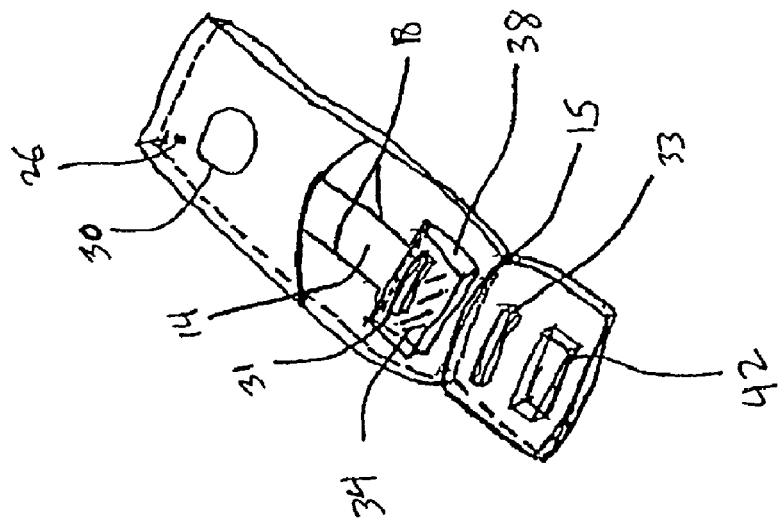

FIG. 17
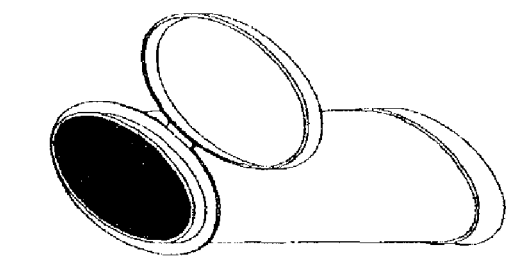
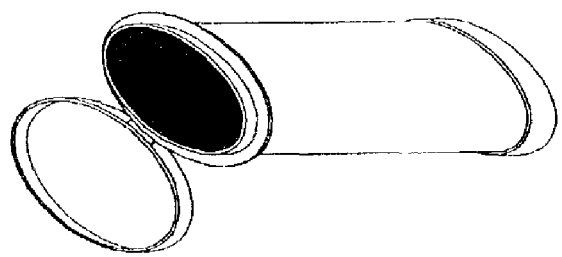
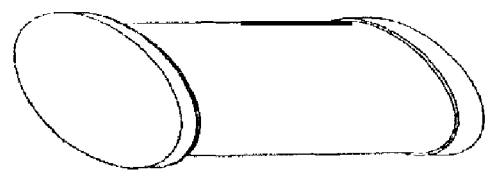

Figure 19
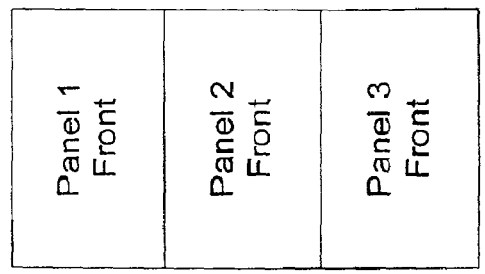
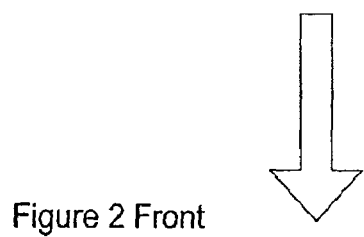
Figure 2 Front
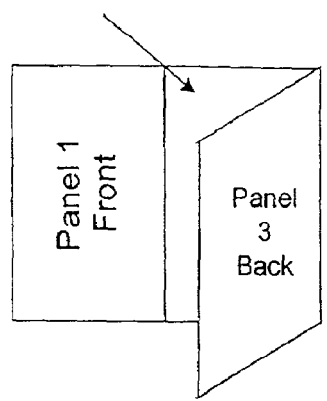
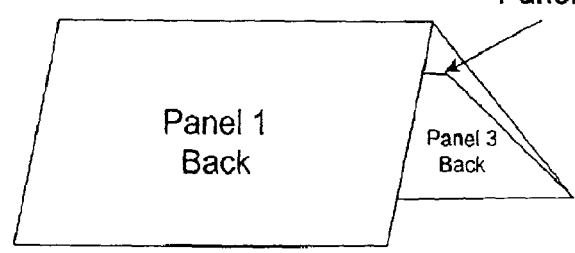

ANALYTE DETECTION

CROSS REFERENCE TO RELATED APPLICATIONS

This application is a continuation of U.S. patent application Ser. No. 09/976,872, Filed: Oct. 12, 2001, now U.S. Pat. No. 7,700,305 B2, Issued: Apr. 20, 2010, which claims priority to U.S. Provisional Patent Application Ser. No. 60/243,854, Filed: Oct. 27, 2000, and is a continuation-in-part of U.S. patent application Ser. No. 09/968,306, Filed: Oct. 27, 2000, now U.S. Pat. No. 6,730,494, Issued: May 4, 2004, and U.S. patent application Ser. No. 09/398,552, Filed: Sep. 17, 1999, now abandoned, each of which are hereby incorporated by reference in their entireties.

FIELD OF THE INVENTION

The present invention relates to analyte detection test systems, including test systems for the oral detection of analytes in saliva. The present invention also provides compositions and methods for storing and distribution of multiple assay tests and compositions and methods for measuring the concentration of analytes in a sample.

BACKGROUND OF THE INVENTION

Advances in detection technologies have made it possible to detect a wide variety of substances in tissue and fluid samples from various organisms. For example, tests are available for qualitative and quantitative detection of glucose, proteins, illicit drugs, cancer markers, cholesterol, pathogens, and other materials in human tissue and fluid samples.

However, many of the available tests are too expensive, cumbersome, complex, or dangerous for routine or frequent usage. For example, many of the tests rely on electronic equipment that is too complex or expensive for use by individuals outside of a laboratory or clinical setting. Additionally, many individuals have an aversion to certain types of sample testing procedures, such as blood and urine testing, and would not be willing to self-administer such assay tests.

The art is in need of detection assay tests for the detection of a wide variety of analytes that adequately combine ease of use, small size, speed, accuracy, low cost, durability (e.g., temperature stability and shelf life), safety and interpretability, and that are designed for widespread distribution and use. Furthermore, delivery systems for packaging, storing, carrying, preserving, and otherwise maintaining tests are needed to provide adequate ease of use, discrete use, accessibility, and durability of tests.

SUMMARY OF THE INVENTION

The present invention relates to analyte detection test systems, including test systems for the oral detection of analytes in saliva. The present invention also provides compositions and methods for storing multiple assay tests and compositions and methods for measuring the concentration of analytes in a sample.

For example, the present invention provides analyte detection assay tests for use in detecting the presence of an analyte in saliva. In some embodiments, the tests are configured for oral use (i.e., at least a portion of the assay test is placed into the mouth and contacted with saliva). In some preferred embodiments, the tests are in the form of a test strip. In some embodiments, the test strip comprises an absorbent reaction pad at one end. In some preferred embodiments, the reaction pad contains reactants that create a detectable signal in the presence of an analyte. In some such embodiments, the reaction pad is configured to produce a detectable signal during or after the placement of the reaction pad into the mouth to collect saliva samples. In some preferred embodiments, the detectable signal comprises the formation of a color. In other preferred embodiments, the detectable signal comprises a change in color.

The present invention also provides a system comprising a plurality of test assays for analyzing a sample for the presence of an analyte. In some embodiments, the system comprises a plurality of assay tests within a delivery system, wherein the delivery system is configured to prevent the assay tests from being exposed to the environment. In some embodiments, the delivery system is configured to dispense the plurality of assay tests individually (e.g., one at a time). In some embodiments, the delivery system is configured to dispense the plurality of assay tests individually without exposing the remaining assay tests (i.e., the tests that have not yet been dispensed) to the environment. In some preferred embodiments, the delivery system comprises a desiccant. In some embodiments, the delivery system comprises a desiccant entrained polymer storage container. In some embodiments, the delivery system is entirely lacking a desiccant.

The present invention further provides a system comprising a diagnostic device for analyzing saliva for the presence of an analyte, with the diagnostic device comprising: a solid support; one or more collection sites attached to a first portion of the solid support, wherein the collection site is configured to collect a saliva sample; one or more reaction sites (e.g., containing agents that produce a detectable signal in the presence of an analyte) attached to a second portion of the solid support, wherein the reaction sites produce a detectable signal in the presence of the analyte; wherein the solid support, collection site, and reaction sites are contained within a single device (i.e., a "lateral flow" device). In some embodiments, no solid support is provided (i.e., the test is made of only a collection site and reaction agents). In some embodiments, the collection site and reaction sites may be in contact with one another (e.g., an absorbent material layered onto or integrated with reaction agents). Thus, in some embodiments the first portion and second portion of the solid support may define partially or entirely overlapping regions of the solid support. In some embodiments of the present invention, multiple collection sites and multiple reactions sites are used. The plurality of collection sites find use, for example, in detecting different threshold concentrations of analyte (e.g., a first collection site that detects 0.4% of analyte in saliva and a second collection site that detects 0.8% of analyte in saliva), different detectable readouts (e.g., different colors or a first collection site that shows a color and a second collection site that produces a symbol, shape, or word), different read-out formats (e.g., a first collection site that uses an on/off readout and a second collection site that uses a gradient readout), different detection purposes (e.g., detection versus indicator [to test if the assay is working properly] or detection of different analytes) and the like.

In some embodiments of the present invention, the diagnostic device comprises a thickness X cm, a width Y cm, and a length Z cm, wherein $X*Y*Z$ is less than 12 cm$^3$, preferably less than 2 cm$^3$ and more preferably less than 1 cm$^3$, although larger and smaller dimensions are also contemplated by the present invention. In some embodiments, the thickness is 1.5 millimeters or less, the length is 5 centimeters or less, and the width is 1.25 centimeters or less. In other embodiments, the solid support comprises plastic. In yet other embodiments, the collection site comprises an absorbent material.

The present invention provides a variety of analyte detection systems. For example, the present invention provides assay tests for use in detecting analytes including, but not limited to, alcohol, glucose, ketones, cancer markers (e.g., prostate-specific antigen [PSA], epidermal growth factor receptor [EGFR], cancer antigen CA 15-3), cortisol, serotonin, 5-hydoxytryptophane, methadone, cocaine, cannabinoids (e.g., 11-carboxy-$\Delta^9$-tetrahydocannabinolic acid), opiates, caffeine, phenytoin, primidone, carbamazepine, antibodies, pathogens (e.g., *P. gingivalis, Chlamydia* organisms, *Streptococcus* organisms, organisms that cause common infectious diseases such as the flu, measles, etc., *Bacillus anthracis* and other organisms that may be used in biological warfare or terrorism, etc.), melatonin, insulin, DHEA sulfate, aldosterone, testosterone, progesterone, andostenedione, estriol, estrone, urea, uric acid, ammonia, calcium, cholesterol, lactoferrin, growth factors (e.g., EGF, NGF, IGF-1), haliperidol, theophylline, cotinine, estradiol, salicyclic acid, acetaminophen, nitrazepam, clobazam, amphetamine, quinine, lithium, antibiotics (e.g., penicillin and tetracycline), vitamins, minerals, toxins, anti-oxidants, monosodium glutamate (MSG), components of food products (e.g., peanuts and/or tree nuts), proteins and nucleic acids (e.g., DNA and RNA), including host and non-host (e.g., pathogenic) proteins and nucleic acids.

In some embodiments, the reaction site comprises an enzyme the reacts directly or indirectly with the analyte to initiate a reaction resulting in the generation of a detectable signal. In some embodiments, the reaction site further comprises one or more competitors, wherein the one or more competitors are configured to prevent the reaction site from producing the detectable signal until the one or more competitors are substantially depleted or otherwise prevent the detectable signal from being substantially detectable unless a threshold concentration of analyte is present in a sample. It is contemplated that, in some embodiments, multiple competitors are used, each with a different threshold level, such that the reaction site produces detectable signals at two or more particular concentrations of test samples. However, it should be noted that, in some embodiments, multiple threshold levels are obtained with the use of a single competitor or no competitors. Indeed, any desired detection configuration can be used. For example, a first detection event may occur at a desired threshold level of analyte, followed by a gradient detection read-out above the threshold level (e.g., a first detected color is observed above a concentration of 0.04%, followed by a gradual increase in a color from concentrations above 0.04%). In some embodiments, the reaction site further comprises one or more stabilizers (e.g., compounds that increase the shelf-life of the reaction site in response to moisture, light [e.g., ultra-violet light], air, and the like). In yet other embodiments, the reaction site comprises two or more reaction components, wherein the two or more reaction components of the reaction site are separated by one or more breakable barriers. In some embodiments, the reaction site is enclosed in a protective encasement.

In some embodiments, the enzyme used in the reaction site is an oxidase or reductase that results in the production of oxidized and reduced reaction products. The oxidized or reduced reaction products result in the generation of a detectable signal through a subsequent oxidation/reduction reaction (e.g., a reaction that results in a color changed cause by a change in the oxidation state of a chromogen). Thus, in some embodiments, any analyte containing a chemical moiety capable of undergoing a change in oxidation state (e.g., analytes containing alcohol, ketone, aldehyde, and/or carboxylic acid groups) finds use with the present invention. The present invention provides non-toxic, non-irritant, and/or non-carcinogenic colorimetric detection systems for use in the reaction site, wherein the color is produced in response to an enzyme (e.g., oxidases, peroxidases, dehydrogenases) that generates oxidized and reduced reaction products (e.g., hydrogen peroxide, $NADP^+$, etc.). These detection systems find use as oral assay tests.

In some embodiments, the assay test employ one or more antibodies that bind to an antigen, wherein the antigen is the analyte to be detected or wherein the antigen is detectable (e.g., generated) when the analyte to be detected is present in a sample. In some preferred embodiments, a colorimetric system is used to indicate the binding between the antibody and the antigen. These detection systems find use as oral assay tests.

In some embodiments of the present invention, the first and second portions of the solid support are separated by a hinge. In other embodiments, the first and second portions of the solid support are separated by a breakable barrier. In yet other embodiments, the collection site is slidingly attached to the solid support. In some embodiments, the collection site and reaction site are provided at the same location.

In some preferred embodiments, the system further comprises a protective encasement, wherein the diagnostic device is enclosed in the protective encasement.

In some preferred embodiments of the present invention, the diagnostic device further comprises a second reaction site attached to a third portion of the solid support, wherein the second reaction site produces a second detectable signal, with the second detectable signal indicating a sufficient volume of the test sample (e.g., saliva sample).

In some embodiments of the present invention, the detection test assay comprises a "test strip" with a thickness X cm, a width Y cm, and a length Z cm, wherein X*Y*Z is less than 12 $cm^3$, preferably less than 2 $cm^3$ and more preferably less than 1 $cm^3$, although larger and smaller dimensions are also contemplated by the present invention. In some embodiments, the thickness is 0.5 millimeters or less, the length is 6.5 centimeters or less, and the width is 5 millimeters or less.

The present invention further provides a system comprising a plurality of test assays for analyzing a sample for the presence of an analyte, said system comprising a plurality of assay tests within a delivery system, said delivery system preventing the assay tests from being exposed to the environment and wherein the delivery system is small (e.g., wallet sized, pocket sized, credit card sized). In some embodiments the small delivery system comprises a width (at the widest portion) of X cm, a length (at the longest portion) of Y cm, and a thickness (at the thickest portion) of Z cm, wherein X*Y*Z is less than 100 $cm^3$ (e.g., 30 $cm^3$ or less, 20 $cm^3$ or less, 10 $cm^3$ or less). In some preferred embodiments, the delivery system is flat (e.g., comprising one or more flat panels). In some such embodiments, the ratios of X:Z and Y:Z are greater than 20:1 (e.g., greater than 30:1, greater than 40:1). In some embodiments, X is 6 cm or less, Y is 8.5 cm or less, and Z is 2 mm or less. In preferred embodiments, the delivery system is configured to dispense the plurality of assay tests individually.

In some embodiments of the present invention, the system further comprises a delivery system, whereby the delivery system comprises one or more compartments capable of storing one or more of the diagnostic devices. In preferred embodiments, the delivery system comprises two or more compartments, each compartment accessible (e.g., independently accessible) to allow use of one or more tests without exposing tests in other compartments. In some embodiments, the delivery system further comprises one or more protective encasements capable of enclosing the diagnostic devices in the one or more compartments. In yet other embodiments the delivery system further comprising one or more placards.

The present invention also provides a delivery system comprising one or more first packages comprising one or more compartments and a second package containing the one or more first packages. For example, in one embodiment, the delivery system comprises one or more assay tests, two or more first packages comprising one or more compartments, wherein the one or more assay tests are contained in the first package; and a second package, wherein the two or more first packages are contained in the second package. For example, in some embodiments, the second package comprises a thin folded delivery system. In some embodiments, the folded delivery system comprises a single fold, wherein the first package is affixed to or contained in a portion of the delivery system such that, in folded form, the first package is enclosed within the folded delivery system. In yet other embodiments, the folded delivery system comprises a pocket, wherein the first package is contained within the pocket. In other embodiments, the folded delivery system comprises two or more folds. For example, in some embodiments, the folded delivery system comprises two folds to provide a three-panel container.

In a particularly preferred embodiment, assay tests are contained in first packages wherein the first packages comprise a first wall and a second wall and wherein each wall comprises at least one layer. In some embodiments, multiple layers are provided. In some embodiments three layers are provided where the inner-most layer comprises an interior heat-sealed protective layer (e.g., a plastic layer), a intermediate "barrier" layer (e.g., a foil, polymer, or polymer film [SARAN, BARAX] layer), and an outer layer (e.g., a paper, cardboard, or polymer layer). In some embodiments, four layers are provided. For example, in some embodiments a "tie" layer is provided between the barrier layer and outer layer (e.g., a plastic or polymer [polyethylene] layer). The first and second wall are connected at the edges to form an interior opening in which the assay test is enclosed (e.g., sealed). In some embodiments, the outer surface of each wall further comprises diagrams, text, or other written materials (e.g., instructions, warning, logo, etc.). In some embodiments, the first packages are contained in second packages. In preferred embodiments, the second package is approximately the size and shape of a credit card. In one preferred embodiment, the second package is made of a first wall and a second wall, wherein the second wall is sealed to the first wall along three edges, forming an opening on one end of the second package. The first packages are insertable and removable through the opening. In particularly preferred embodiments, the first wall of the second package is transparent to allow viewing of the contents (e.g., viewing of written materials on the first packages contained within the second package). In other preferred embodiments, the second package is made of plastic. In yet other preferred embodiments, the second package contains two or more first packages (e.g., to allow users to access assay tests on more than one occasion).

In other embodiments, the second package comprises a first and second wall connected by a hinge along one edge of the first and second walls. Assay tests are attached to the inner surface of the first wall (e.g., enclosed in a pouch contained on the inner surface of the first wall). When the hinge is closed, the assay tests are enclosed between the first and second walls. When the hinge is opened, the assay tests are accessible.

In yet another preferred embodiment, the delivery system further comprises a flat solid support and one or more first packages (each containing one or more assay tests in one or more compartments) attached (e.g., glued) to the flat solid support. In a preferred embodiment, the first packages are attached to the solid support in such a manner that the assay tests are accessible without removing the first package(s) from the solid support.

The present invention also provides a delivery system for storing assay tests, comprising one or more (e.g., two or more) compartments configured to contain assay tests. In some preferred embodiments, the delivery system further comprises a plurality of protective encasements capable of enclosing the assay tests in the compartments. In other preferred embodiments, the delivery system comprises a thickness, a width, and a length, wherein the thickness is 2 millimeters or less, the length is 6.0 centimeters or less, and/or the width is 8.5 cm or less. In yet other preferred embodiments, the delivery system has a thickness less than 1 millimeter, a length less than 8.5 centimeters, and/or a width less than 5.6 cm. In yet other preferred embodiments, the delivery system is the approximate size and shape of a standard credit card. In yet other preferred embodiments, the delivery system further comprises one or more placards.

While the present invention is not limited by the materials used in the delivery system, in some preferred embodiments, the delivery system is made of plastic or a paper or cardboard material. In some embodiments, the paper or cardboard material comprises laminated paper or cardboard.

The present invention further provides a delivery system for storing assay tests, comprising one or more (e.g., two or more) compartments and one or more assay tests, wherein the one or more assay tests are contained within the one or more compartments. In preferred embodiments, the delivery system comprises two or more compartments, each containing one or more assay tests. In some preferred embodiments, the delivery system further comprises a plurality of protective encasements, wherein the protective encasements enclose the one or more assay tests in the compartments. In other preferred embodiments, the delivery system comprises a width (at the widest portion) of X cm, a length (at the longest portion) of Y cm, and a thickness (at the thickest portion) of Z cm, wherein $X*Y*Z$ is less than 100 cm$^3$ (e.g., 30 cm$^3$ or less, 20 cm$^3$ or less, 10 cm$^3$ or less). In some preferred embodiments, the delivery system is flat (e.g., comprising one or more flat panels). In some such embodiments, the ratios of X:Z and Y:Z are greater than 20:1 (e.g., greater than 30:1, greater than 40:1). In some embodiments the thickness is 2 millimeters or less, the length is 5.5 centimeters or less, and/or the width is 8.25 cm or less. In yet other preferred embodiments, the delivery system has a thickness less than 1 millimeter, a length less than 8.5 centimeters, and/or a width less than 5.5 cm. In yet other preferred embodiments, the delivery system is the approximate size and shape of a standard credit card. In yet other preferred embodiments, the delivery system further comprises one or more placards. In other embodiments, the delivery system comprises plastic.

In some preferred embodiments, the delivery system comprises a protective storage container comprising a round or oval vial with a thickness, a width, and a length. While the present invention is not limited by the dimensions of the container, in preferred embodiments, the thickness is X millimeters or less, the length is Y centimeters or less, and the diameter is Z cm or less wherein $X*Y*Z$ is less than 15 cm$^3$, preferably less than 10 cm$^3$. In some embodiments, the thickness is 5 millimeters or less, the length is 5 centimeters or less, and the diameter is 2.5 cm or less. In other embodiments, the delivery system is a round or oval vial made of a thermoplastic polymer with an entrained desiccant that removes moisture from the interior of the container. In some embodiments of the present invention, the system further comprises a delivery system, whereby the delivery system comprises a protective storage container having one or more compartments capable of storing one or more of the assay tests. In preferred embodiments, the storage container has a cap providing an air tight seal and connected by a hinge of the same said polymer material wherein said cap, hinge and container are molded as one piece. In still more preferred embodiments the storage container is made of a hard thermo-plastic polymer with an entrained desiccant allowing for easy accessibility without jeopardizing the reaction means to environmental moisture or humidity.

DESCRIPTION OF THE FIGURES

FIG. 8 shows an assay test made with a hinge that allows two pieces from one end of an assay test to be folded around the other end.

FIG. 9 shows an assay test made with a sliding mechanism that allows a portion from one end of an assay test to be slid around the other end.

FIG. 12a shows an assay test from FIG. 1 and how it fits into a protective encasement.

FIG. 12b shows a delivery system that stores multiple assay tests and is made with multiple compartments that are each covered with a removable protective encasement.

FIG. 13c shows an assay test similar to the assay test in FIG. 1, but which comprises a secondary chamber containing additional reaction components.

FIG. 13d shows an assay test similar to the assay test in FIG. 13c, but which comprises two main components instead of three.

FIG. 17 shows one embodiment of the delivery systems of the present invention.

FIG. 19 shows a folded delivery system in one embodiment of the present invention.

GENERAL DESCRIPTION OF THE INVENTION

Figure 2:
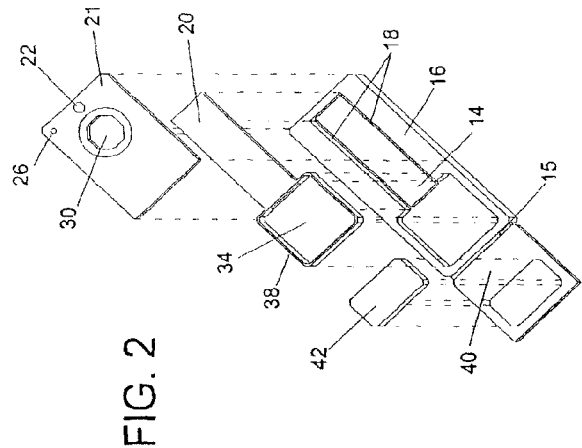
FIG. 2 shows the three main components that make up the assay test in FIG. 1.

The present invention relates to assay test systems, including compositions and methods for storing multiple assay tests and compositions and methods for measuring the presence of or concentration of analytes in a sample. In preferred embodiments, the present invention provides:

1) An assay test that comprises a single device so that it is easy to use. In preferred embodiments, the assay test is also small, fast, accurate, inexpensive, safe, easy to read and decipher, and durable; and
2) A delivery system that stores multiple assay tests so that the assay tests can be accessed on one or more occasions. In preferred embodiments, the delivery system makes assay tests both easy to carry and durable. In some preferred embodiments, the delivery system comprises a protective storage container providing a cap with an air tight seal and a plug, sleeve, pouch, liner, or other material comprising an entrained desiccant that removes moisture away from the contents of the container. In other preferred embodiments, the delivery system comprises a folded structure, wherein assays test are attached or enclosed in an interior portion of the folded structure. In preferred embodiments, the delivery system is small and portable to allow ease of handling.

Preferred embodiments of the present invention provide tests and systems that facilitate wide-spread use of assay tests by individuals. For example, the present invention provides assay tests that are contained within a single device and are easy to use, small, fast, accurate, reliable, inexpensive, easy to read and decipher and durable. In preferred embodiments, multiple tests are contained in a delivery system such that one or more tests can be accessed and used at separate times.

Thus, in some embodiments, the assay test of the present invention comprises a single device so that it is easy to use. In preferred embodiments, the assay test is small so that it is easy to carry. In some preferred embodiments, the assay test works fast so people do not have to wait long before obtaining the results. In other preferred embodiments, the assay test is accurate so individuals can make decisions based on correct information. In yet other preferred embodiments, the assay test is reliable so people know when it is functioning properly. In some embodiments, reliability is provided by assay tests that have undergone sufficient quality control and assessment to provide highly accurate and consistent results. In some embodiments, the assay test includes an indicator to identify, upon use, if the test is reliable. In some preferred embodiments, the assay test is inexpensive so that it can be afforded easily. In still other preferred embodiments, the assay test is durable so that it can be handled easily without breaking or becoming damaged. Unlike currently available detection devices, the assay tests of the present invention combine these desired features into a single, easy to use test that significantly facilitates self-detection and assessment of analytes.

The present invention further provides delivery systems that a) store multiple assay tests so that they can be accessed on one or more occasions (e.g., on one or more separate days, weeks, or months), b) in some embodiments, make assay tests durable and easy to access and carry, and c) in some other embodiments, provide placards for instructions, warnings, labels, and other text or diagrams. As mentioned above, the delivery systems of the present invention store multiple assay tests so that multiple assay tests can be accessed on a single occasion or on two or more distinct occasions. This flexibility is important for several reasons. For example, because individuals may use assay tests on separate occasions, the delivery system stores a sufficient quantity of tests to last an individual a period of days, weeks or months, thereby diminishing the need to continually replenish assay test supply. Additionally, because individuals may use more than one tests on a given occasion, for example, to determine if their analyte concentration has dropped over time, the delivery system stores multiple assay tests.

In preferred embodiments of the present invention, the delivery system makes assay tests easy to carry so that individuals can easily and discreetly put the assay tests in their pockets, wallets, or purses for use in situations away from home. In other preferred embodiments, the delivery system ensures the durability of the assay tests by enclosing them in a protective hard container. In some preferred embodiments, the container comprises a plastic-polymer container with an entrained desiccant. Such a protective container assures that the assay tests do not break or spoil due to a breakdown or degradation of the biosensor, enzymes, antibodies, antigens, colorimetric agents, or other reaction agents. In yet other preferred embodiments, the delivery system makes assay tests easy to access so that removal of the assay test from the delivery system can be conveniently accomplished, even by impaired individuals. Thus, in some embodiments of the present invention, an assay test is dispensed upon opening the delivery system, while the remaining tests are maintained in the delivery system (e.g., maintained so as not to be exposed to the environment). In some preferred embodiments, the delivery system provides large placards so that instructions, labels, warnings, or other text or diagrams are easy to notice and read. The assay tests, first package, or second package may also contain such information.

The present invention further contemplates assay tests and delivery systems that provide advantages for distribution of the tests and systems to individual consumers by one or more secondary parties (i.e., parties other than the consumer). For example, it is contemplated that the assay tests are provided to consumers by another party (e.g., a restaurant, bar, university, insurance company, employer, government agency, etc.). In such embodiments, it is contemplated that multiple assay tests are provided to the consumer so that testing can occur on more than one occasion to avoid distribution each time the consumer needs the test. Thus, in some embodiments of the present invention, it is desired to have delivery systems comprising multiple assay tests that can be accessed on one or more occasions. In other embodiments, it is desired to have a protective container made of a thermoplastic polymer with an entrained desiccant such that excess moisture is removed from the tests contained therein.

In some embodiments of the present invention, materials other than the assay tests are further included in or on the delivery systems. For example, in some embodiments, the delivery system or assay test comprises an image or text associated with a company, agency, or individual other than the provider of the assay test in order to obtain the positive image associated with the assay tests of the present invention (i.e., co-branding). The co-branding may be provided on the surface or interior of the delivery systems, may be included on materials attached to the delivery system, or may otherwise be associated with the delivery system. In embodiments of the present invention where multiple assay tests are provided in a delivery system for use over a period of time, the co-branding provides constant and long-term advertising for the entity providing the co-branding since the consumer is in possession of the delivery system on their person for extended periods of time.

In other embodiments of the present invention, the delivery system further comprises information or safety materials attached to, within, on, or otherwise associated with the delivery systems. Such materials include, but are not limited to, information for transportation services (e.g., taxis, buses, etc.) and emergency services (e.g., police, hospital, etc.). In some embodiments, the materials comprise items that help individuals pass the time (e.g., while waiting for an analyte level to increase or drop) including, but not limited to, puzzles, games, Internet access devices, etc (i.e., "time-consuming materials"—materials other than the assay test or delivery system that can be used to occupy an individual's time for minutes to hours). In other embodiments, phone cards (e.g., pre-paid phone cards) or dial-in numbers are provided to allow the individual to arrange transportation or pass time. In still further embodiments, the materials comprise rebates or coupons for products, and/or samples of a product. In yet other embodiments, the materials comprises information related to awareness of physical, mental, and/or social problems related to the analyte.

Definitions

To facilitate an understanding of the present invention, a number of terms and phrases are defined below:

As used herein, the terms "assay test system," "assay test," and "diagnostic device" refer to any system capable of determining, either quantitatively or qualitatively, the presence of or concentration of an analyte in a sample. Such assay test systems include both detection assay tests themselves (e.g., devices or combinations of devices that contain sample collection and analyte detection capabilities) and any associated "delivery systems" (i.e., systems used to store, transport, and maintain assay tests and other items). In some preferred embodiments, the "test assay" comprises a simple test strip containing a reactive site at one end, such that the reactive site provides a detection element in the presence of analyte when exposed to a sample suspected of containing analyte.

As used herein, the term "sample" is used in its broadest sense. In one sense it can refer to a saliva sample. In another sense, it is meant to include a specimen or culture obtained from any source, including biological and environmental samples. Biological samples may be obtained from animals (including humans) and encompass fluids, solids, tissues, and gases. Biological samples include blood products (e.g., plasma and serum), saliva, urine, lachrymal fluid, cell lysates and the like. Environmental samples include environmental material such as surface matter, soil, water, and industrial samples. These examples are not to be construed as limiting the sample types applicable to the present invention.

As used herein, the terms "reaction means," "reaction agent," and "reaction site" refer to compositions that provide for a reaction. For example, reaction means include, but are not limited to: enzymes, cofactors, and buffers for enzymatic reactions; ligands, analytes, or biosensors; and any other composition that facilitates a reaction. For example, where the analyte is an alcohol (e.g., methanol, ethanol etc.), in one embodiment of the present invention, the reaction means comprises an alcohol dehydrogenase, NAD(P)H and/or NADH cofactors, a diaphorase, and a chromogen for colorimetrically detecting the presence of alcohol in a sample. In another embodiment, the reaction means comprises an alcohol oxidase. The term "biosensors" refers to any sensor that is partially or entirely composed of biological molecules. In a traditional sense, the term refers to "an analytical tool or system consisting of an immobilized biological material (such as enzyme, antibody, whole cell, organelle, or combination thereof) in intimate contact with a suitable transducer device which will convert the biochemical signal into a quantifiable electrical signal" (Gronow, Trends Biochem. Sci. 9: 336 [1984]). However, as used herein, the term biosensor is not limited to the incorporation or association with transducer devices. The present invention contemplates biosensors with and without transducer devices.

As used herein, the term "immobilization" refers to the attachment or entrapment, either chemically or otherwise, of material to another entity (e.g., a solid support, substrate, or surface) in a manner that restricts the movement of the material.

As used herein, the terms "solid support," "solid substrate," and "solid surface" refer to any material that provides a solid or semi-solid structure with which another material can be attached. Such materials include smooth supports (e.g., metal, glass, plastic, silicon, and ceramic surfaces) as well as textured and porous materials. Such materials also include, but are not limited to, gels, rubbers, polymers, and other non-rigid materials. Solid supports need not be flat. Supports include any type of shape including spherical shapes (e.g., beads). Materials attached to solid support may be attached to any portion of the solid support (e.g., may be attached to an interior portion of a porous solid support material). For example, solid supports include, but are not limited to, plastic, ceramic, paper, cardboard, or metal supports structures for supporting or enclosing collection sites, reactions means, or other compositions. In some embodiments, solid supports may further comprise other materials (e.g., desiccants).

As used herein, the term "collection site" refers to a portion of a composition capable of collecting a sample. Collection sites include, but are not limited to, hydrophilic pads, porous membranes, films, patches, polymers (e.g., silicone, rubber, acrylics), and absorbent materials. For examples, collections sites include, but are not limited to, polypropylene, polyethylene, polystyrene, polyester, polyacrylates and methacrylates, polyacrylamide, polyisobutylene (synthetic rubbers), starch, and cellulose (See e.g., U.S. Pat. No. 5,585,273, herein incorporated by reference in its entirety). The term "absorbent material" includes, but is not limited to, cotton or other thin fiber-based material, paper (e.g., filter paper), cloth, sponge, and other absorbent materials.

As used herein, the term "alcohol metabolizing enzymes" refers to any enzyme capable of reacting with an alcohol substrate. Alcohol metabolizing enzymes include but are not limited to alcohol dehydrogenases and alcohol oxidases.

As used herein, the term "enzyme" refers to molecules or molecule aggregates that are responsible for catalyzing chemical and biological reactions. Such molecules are typically proteins but can also be short peptides, RNAs, or other molecules.

As used herein, the term "competitor" refers to an any means capable of reducing the rate of a reaction. In some embodiments, competitors include, but are not limited to competing substrates that compete with another substrate for access to an enzyme active site. The competing substrate may have greater or lessor affinity for the active site than the other substrate. In other embodiments, competitors include, but are not limited to trapping agents that prevent a substrate from reacting with an enzyme or prevent a reaction product from being detected.

As used herein, the term "substantially depleted" refers to a competing substrate that has reacted with an enzyme to such a degree that other substrates are capable of accessing the enzyme at significant levels (e.g., detectable levels).

As used herein, the term "sol-gel" refers to preparations composed of porous metal oxide glass structures. Such structures can have biological (e.g., enzymes) or other material entrapped within the porous structures. The phrase "sol-gel matrices" refers to the structures comprising the porous metal oxide glass with or without entrapped material. The term "sol-gel material" refers to any material prepared by the sol-gel process including the glass material itself and any entrapped material within the porous structure of the glass. As used herein, the term "sol-gel method" refers to any method that results in the production of porous metal oxide glass. In some embodiments, "sol-gel method" refers to such methods conducted under mild temperature conditions. The terms "sol-gel glass" and "metal oxide glass" refer to glass material prepared by the sol-gel method and include inorganic material or mixed organic/inorganic material. The materials used to produce the glass can include, but are not limited to, aluminates, aluminosilicates, titanates, ormosils (organically modified silanes), and other metal oxides.

As used herein, the term "direct colorimetric detection" refers to the detection of color changes without the aid of an intervening processing step (e.g., without conversion of a color change into an electronic signal that is processed by an interpreting device). It is intended that the term encompass visual observing (e.g., observing with the human eye).

As used herein, the term "chromophore" refers to molecules or molecular groups responsible for the color of a compound, material, or sample.

As used herein, the term "aqueous" refers to a liquid mixture containing water, among other components.

As used herein, the term "breakable barrier" refers to a barrier between chambers or wells that can be broken, for example, by bending, compressing, heating, snapping, twisting, or other disruptions, such that the contents of the chambers or wells have access to one another.

As used herein, the term "indicator" refers to a detectable signal that indicates the introduction of sufficient sample to a reaction means for a desired (e.g., detectable and reliable) reaction to take place.

As used herein, the term "protective encasement" refers to a thin covering, wrapping or shielding comprising a material that acts to protect a composition such as a reaction means (e.g., to extend the shelf-life of the reaction means).

As used herein, the term "communication facilitating agent" refers to an agent that allows an individual to initiate a communication with another individual or with another entity. Communication facilitating agents include, but are not limited to, phone cards, pre-paid dial-in phone numbers, Internet access information, etc. that allow one to initiate a communication with another party (e.g., a party capable of providing the individual transportation).

As used herein, the term "low-moisture environment" refers to environments with a lower moisture content then the ambient environment.

Figure 14:
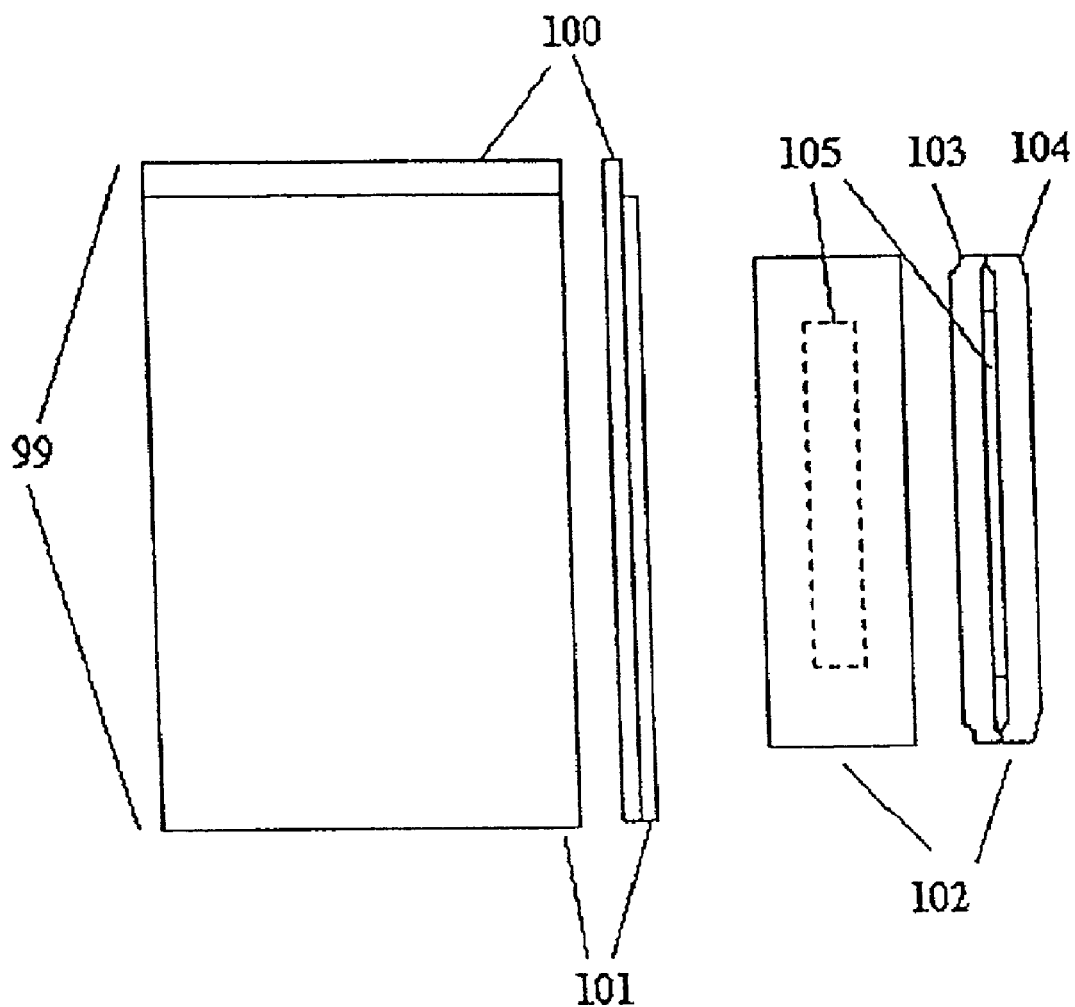
FIG. 14 shows one embodiment of the delivery systems of the present invention.

As used herein, the term "sleeve," when referring to delivery systems, refers to a pouch-like enclosure comprising at least two, preferably three, sealed sides to provide an opening for the insertion, removal, enclosure, and storage of another item. In some preferred embodiments, the sleeve is contained on a credit-card sized delivery system (e.g., approximately 9 cm×6 cm×2 mm). One embodiment of such a sleeve containing delivery system is shown in FIG. 14. The sleeve portion of the delivery system may be made of any material, including, but not limited to, plastic, paper, cardboard, and the like.

As used herein, the term "entrained" refers to materials that are integrated, attached, or in fixed contact with other materials. For example, entrained desiccants are desiccants that are mixed within another material or attached or fixed to another material (e.g., attached or fixed as a lining within a container).

As used herein, the term "time-consuming materials" refers to materials other than assay tests or delivery systems that can be used to occupy an individual's time (e.g., for minutes to hours). Such materials may comprise objects or may be written material or other text. Such written material may, is some embodiments, be included on assay tests or delivery systems. Examples of time-consuming materials include, but are not limited to puzzles, games, Internet access devices. Time consuming materials find use, for example, in passing time while waiting for one's blood alcohol concentration to drop.

DETAILED DESCRIPTION OF THE INVENTION

The present invention provides systems for determining the presence of or level of an analyte in a sample. For example, the present invention provides qualitative and quantitative detection assays that determine if an analyte is present in a sample at or above one or more specific concentration levels.

In preferred embodiments of the present invention, the test assay comprises an oral test assay. In particularly preferred embodiments, the test assay is an easy-to-use test strip comprising a reaction site at one end. In some preferred embodiments, the reaction site is place into the mouth of an individual and is saturated with saliva. If the targeted analyte is present in the saliva, a detectable signal is produced, indicating the presence of, or concentration of, the analyte. In some preferred embodiments, the detectable signal is detectable by the human eye (e.g., a viewable color change). However, the present invention includes detectable signals that are read by a device. Because the reaction site is placed in the mouth, it is preferred that components of the reaction site are non-toxic, non-irritant, non-carcinogenic, and otherwise do not produce any undesired or inconvenient physical reactions in the user.

The following description highlights several preferred embodiments of the present invention. The present invention is not limited to these illustrative examples. While the following description highlights the use of test strips for oral use, it should be understood that the other configurations are within the scope of the present invention. The detailed description is provided in the following sections: I) Assay Tests; II) Delivery Systems; and III) Analytes.

I. Assay Tests

A. Description

Figure 18:
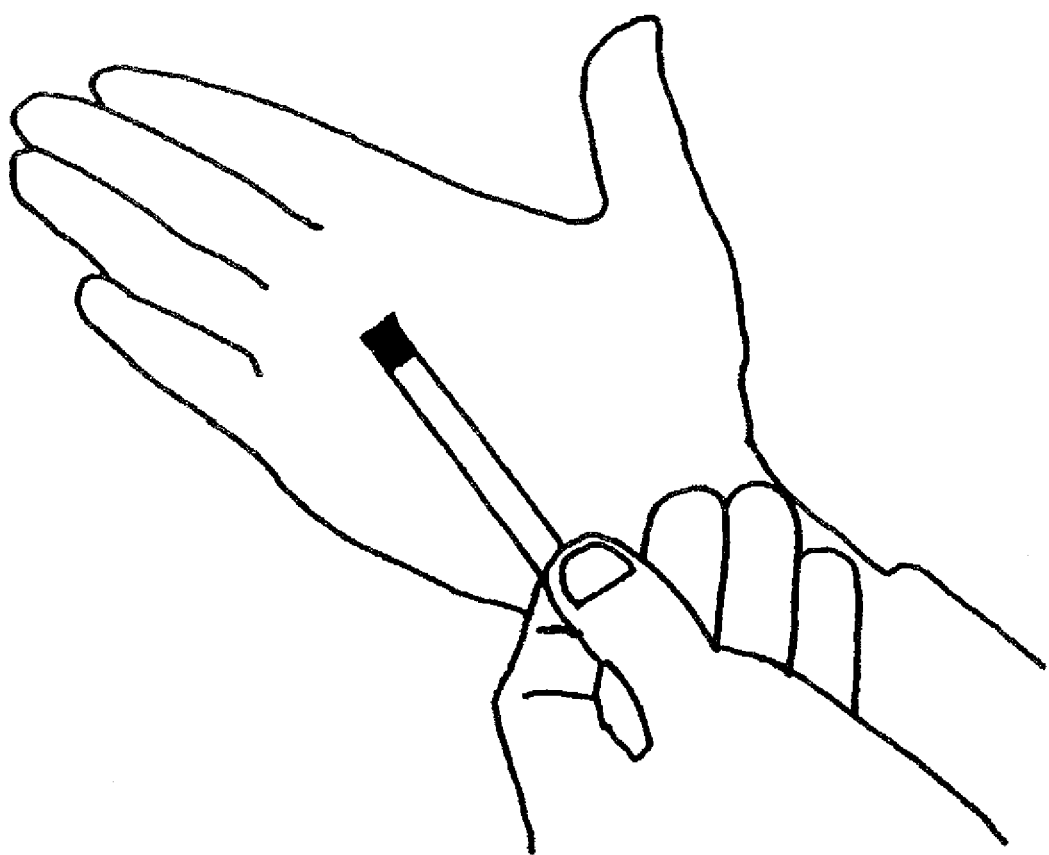
FIG. 18 shows an assay test strip in one embodiment of the present invention.

The assay test is preferably small in size so that it can be easily carried. For example, in some embodiments, the assay test forms a 'strip' and is rectangular, flat, and thin, such that multiple assay test strips can be stored in a delivery system that is convenient to carry. An example of a test strip in one embodiment of the present invention is shown in FIG. 18.

In preferred embodiments, the components of the assay test of the present invention are contained within a single device so that it is easy to use. The assay tests comprises three main components: a solid support, a collection site and a reaction means. In some embodiments, the assay tests comprise a desiccant material.

1. Solid Support

The assay test comprises a solid support providing both a handle or free end to hold the test with as well as providing a substrate for other compositions (e.g., collection site). In embodiments where the assay test comprises a test strip, the solid support is typically a thin paper, filter, or plastic material wherein one end of the strip provides the free end to hold, while the other end of the strip contains the collection site and reaction means. In some embodiments, the solid support comprises a desiccant material.

2. Collection Site

The assay test comprises a collection site for collecting a sample. In some embodiments of the assay test, the collection site comprises an absorbent material that can absorb a sample (e.g., a fluid such as saliva) from an individual. In some embodiments, the sample flows from the absorbent material to a reaction means (e.g., by diffusion), while in other embodiments the collection site is physically introduced near a reaction means such that the sample is introduced to the reaction means. In yet other embodiment, the reaction means and collection site are in contact with one another or are integrated. Several assay test formats that allow the introduction of the sample from an absorbent material to a reaction means are described below. In other embodiments of the present invention, a sample is directly introduced into a reaction means without an absorbent material (e.g., by introduction of fluid into a collection site comprising a well or chamber).

In some embodiments, the assay test is provided with a stimulator, configured to stimulate saliva production in the mouth. These embodiments are employed, where it is desired or necessary to have large volumes of saliva or where newly produced saliva provides a more accurate correlation to blood concentrations of analyte (e.g., for glucose detection). Any physical (e.g., a physical protrusion the enters the mouth and provokes salivation), psychological (e.g., images or scents the stimulate salivation), or chemical (e.g., saliva stimulation tablets that do not interfere with the detection chemistry; flavors) methods for stimulating saliva production are contemplated.

3. Reaction Means

The assay test further comprises a reaction means for detecting the presence of analyte in a sample. A wide variety of reaction means are compatible with the present invention. Acceptable reaction means are those that can be incorporated into the assay tests of the present invention and that can maintain a detectable signal in the presence of analyte. Reaction components that find use in the detection of particular analytes are described in Section III, below. In some embodiments, the reaction means comprises an enzyme that reacts with the analyte, directly or indirectly, to generate a reaction product that is directly or indirectly detected. For example, enzymes that react with analytes and produces an oxidized or reduced reaction product find use in the present invention. In some embodiments, the oxidized or reduced product is used is a reaction with a chromogen to produce a visibly detectable color. In some embodiments, a series of reactions are used to amplify the signal. For example, reaction products of a first reaction are each used to generate multiple reaction products in a second reaction. The reaction products of the second reaction are then used in subsequent reactions, eventually leading to the generation of detectable response.

In some embodiments, the reaction means provides a qualitative measurement of analyte concentration. In some embodiments, the presence of a detectable signal indicates the presence of an analyte, without indicating a specific amount of the analyte. In other embodiments, the detectable signal appears when a particular threshold analyte concentration is present. While this indicates that the concentration of analyte is above a certain concentration, it does not provide a quantitative measure of actual analyte concentration. In some embodiments, the detectable signal (e.g., color) increases with increasing analyte concentration. An estimate of analyte concentration is made by comparing the level of detectable signal to a chart or table representing ranges of analyte concentration that correspond to an approximate level of detectable signal. In some embodiments, the detectable signal is measured to determine a quantitative amount analyte in the sample. In some embodiments, one or more control test assays are used to assist in quantitative determination (e.g., a second test assay is used on a sample with known analyte concentration).

In other embodiments, of the present invention, a biosensor is used. A wide variety of biosensors find use in the reaction means of the present invention, including, but not limited to the biosensors described in U.S. Pat. Nos. 5,571,395, 5,792,621, 5,500,351, and 6,183,772, incorporated herein by reference in their entireties. In some embodiments, the biosensor employs an antibody. In some embodiments of the present invention, the reaction means provide a colorimetric response that intensifies with increasing concentrations of analyte (e.g., a gradient reading). In alternate embodiments, the reaction occurs at one particular or multiple threshold levels, as desired (See e.g., U.S. Pat. No. 5,032,506, incorporated herein by reference in its entirety).

In some embodiments that require a series of chemical reactions to take place in sequence, the assay test further comprises multiple chambers for separating, isolating, combining, or storing the reaction components. For example, when a chemical is stored dry, but active only in aqueous solution, separate chambers store the chemical and aqueous solution. Directly prior to or during use of the assay test, the contents of the chambers are combined (e.g., by breaking a barrier separating the separated components).

In some embodiments of the present invention, the reaction means is immobilized to increase durability, accuracy, and ease of use. For example, in some embodiments the reaction means is immobilized on filter paper, or another material, which allows transfer of the sample to the reaction means and provides a reflective surface for enhanced colorimetric detection. The reaction means may also be immobilized in chambers or in gels. In some embodiments of the present invention, the reaction means is immobilized in a porous metal oxide matrix using the sol-gel method (See generally, Brinker and Scherer, Sol-Gel Science, Academic Press, San Diego [1995]). Sol-gel entrapment provides cost-efficient, stable, accurate, reliable, consistent, and robust materials that can be produced in a variety of shapes and sizes. The unique properties of sol-gel materials such as optical transparency, durability, and tailorable properties (e.g., porosity, surface functionalization, thin films, and bulk materials) provide an ideal material for immobilization of colorimetric materials. The sol-gel process has been used for entrapping organic molecules such as dyes and proteins in silica gels (See e.g., Avnir, Accounts Chem. Res. 28: 328 [1995]; Yamanaka et al., Am. Chem. Soc. 117: 9095 [1995]; Miller et al., Non-Cryst. Solids 202: 279 [1996]; and Dave et al., Anal. Chem. 66: 1120A [1994]).

In particularly preferred embodiments, the assay test further comprises an indicator that comprises a second reaction means. The indicator provides a detectable signal indicating the introduction of sufficient sample to the first reaction means for a reaction to take place, ensuring the reliability of the assay test. Several of such preferred embodiments are described in detail below. For example, in one embodiment of the present invention, the indicator is located at the end of a sample path, downstream of the first reaction means. The sample must pass through the first reaction means before reaching the indicator. By providing the indicator with a second reaction means, a positive result with the indicator demonstrates that a sufficient amount of sample has been exposed to the first reaction means. In some embodiments, the indicator employs the same chemistry as the primary assay reaction site, while in other embodiments scavengers are excluded and/or a different chromogen is used (independent of toxicity, irritability, or carcinogenicity if the indicator is not exposed to the user).

In other preferred embodiments, the assay test comprises a protective encasement. In some embodiments, the protective encasement comprises a material such as foil and covers the reaction means. In such embodiments, the protective encasement is automatically broken and reveals the reaction means when the user operates the assay test. In still other embodiments, the protective encasement comprises a material such as foil and surrounds the entire assay test. In such embodiments, the user opens the protective encasement to reveal the assay test before operating the assay test.

B. Operation

In one preferred embodiment of the present invention, a protective storage container is opened to reveal an assay test. The assay test operates by first saturating an absorbent material on one end of the assay test with a sample. Depending on the reaction means used in the assay test, the user waits for a period of time and interprets the detectable signal produced by the reaction means. In embodiments that employ an indicator, to check the reliability of the assay test, the user observes if enough sample was initially put on the absorbent material by viewing a detectable signal from the indicator. The absence of a detectable signal from the indicator demonstrates that not enough sample was initially put on the absorbent material, and that the test may not be reliable. Finally, the user checks their analyte concentration by viewing a color change or other detectable signal (e.g., the appearance of a symbol such as a shape or word) from the reaction means. In some embodiments, to make the assay test easy to decipher, the user compares the color changes to pictorial and written instructions printed on the assay test or a delivery system.

In another preferred embodiment of the present invention, a protective encasement is opened to reveal an assay test. The assay test operates by first saturating an absorbent material on one end of the assay test with a sample. The user then, in one-step, either (1) folds or slides this saturated end into a well on the second region of the assay test, or (2) folds or slides pieces from a second region of the assay test around or onto the saturated end. In preferred embodiments, the folding or sliding motion is designed for quick and easy use. Detection is carried out as described above.

In some preferred embodiments where an enzyme is used as part of the reaction means, the portion of the test assay containing the reaction means (e.g., a pad on a test strip) is maintained in the mouth of a subject for an extended period of time (e.g., for 5 seconds to several minutes), as the enzymatic reaction proceeds at a higher rate at the elevated temperature in the mouth. This method is in contrast to methods where the test assay is briefly saturated with the saliva and then incubated at room temperature until color development. Where the enzymatic reaction is allowed to occur in the mouth, the entire reaction time from initial testing to detecting the presence or absence of a color change is carried out in less time. The increased speed for reading the assay increases the likelihood that the assays will be used.

Figure 1:
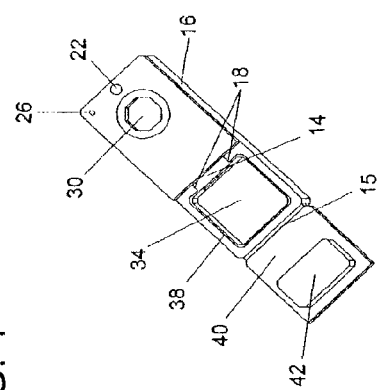
FIG. 1 shows a top view of an assay test made with a hinge that allows one end of a test to be folded onto the other.

One embodiment of the alcohol concentration assay test of the present invention is illustrated in FIG. 1. The assay test is approximately 1.5 mm in thickness, and has overall dimensions of roughly 5 cm×1.25 cm, although both larger and smaller dimensions are contemplated and can be designed, as desired (e.g., a thickness X cm, a width Y cm, and a length Z cm, wherein X*Y*Z is less than 12 cm$^3$, preferably less than 2 cm$^3$ and more preferably less than 1 cm$^3$).

FIG. 2 illustrates the assay test components of the assay test shown in FIG. 1. The assay test comprises three main parts, a base 16, a middle 20, and a top 21. The base 16, middle 20, and top 21 are constructed of a strong, durable material such as plastic, although a variety of materials are contemplated by the present invention. In this figure, the attachments to the base 16 include a hinge 15, two filter avenues 18, a well covering 40, an absorbent material 42, and a reaction means impregnated on a thin sheet 14 for detecting the presence of alcohol in a sample. The hinge 15 is constructed in conjunction with the base 16 to form a single molded part. The hinge is made of a thin, flexible material such as plastic, although a variety of materials are contemplated by the present invention. The hinge 15 allows the well covering 40 to easily fold, snap, and lock onto the well 38 on the middle section 20. The hinge 15 also allows the absorbent material 42 to easily fold into the well 38. The filter avenues 18 allow the fluid sample from the absorbent material to travel up both sides of the base 16. A material or body that draws a fluid sample such as filter paper or small capillary tubes is used to construct the filter avenues 18. The well covering 40 is constructed in conjunction with the base 16 to form one molded part. The absorbent material 42 is constructed of a material that absorbs and collects a desired fluid sample (e.g., saliva) such as a synthetic sponge or cotton fibers, although a variety of materials are contemplated by the present invention. The sheet 14 comprises either: (a) a pre-established, fast, inexpensive, and accurate chemical reaction means which produces a controlled color change, (b) a pre-established, fast, inexpensive, and accurate biosensor which produces a controlled color change, or (c) any other accurate, inexpensive, and fast technology that reacts in the presence of analyte to produce a controlled detectable signal (e.g., a color change).

The attachments to the middle 20 include a well 38 and a porous membrane 34. The well 38 is constructed in conjunction with the middle 20 to form one molded part. The well 38 is made so that the absorbent material 42 compresses to fit snugly inside. In addition, the well 38 is constructed so that the well covering 40 snaps and locks on top of the well 38. The membrane 34 is located at the bottom of the well 38. It is made of a porous material that allows the fluid sample to pass but does not allow other debris to pass.

The attachments to the top 21 include a small window 22, large window 30, and air hole 26. The two windows 22 and 30 are open or transparent spaces that allow the sheet 14 to be viewed through the middle 20. The air hole 26 is a hole in both the top 21 and the middle 20 which allows air to escape from the base 16.

II. Delivery Systems

A. Description

The present invention provides delivery systems for assay tests that store one or more assay tests so that assay tests can be accessed on a single occasion or on two or more distinct occasions. In some embodiments, the delivery system also comprises a protective storage container making assay tests both durable and easy to access, carry, and distribute, and, in other embodiments, comprises placards that allow instructions, labels, warnings or other text or diagrams to be easily noticed and read. In still other embodiments, the delivery systems comprises additional materials, including but not limited to, co-branding materials, phone cards, etc, as described above.

The delivery system of the present invention is preferably small in size so that it can be easily carried. For example, in some embodiments, the storage container is rectangular, flat, and thin (e.g., shaped like a credit card), while in other embodiments the container is round, oval, or other shapes as shown in FIG. 17 (e.g., with a height of approximately 5 cm or less and a diameter of approximately 2.5 cm or less), such that individuals can easily and discreetly carry the delivery systems in their pockets, wallets, or purses for use in situations away from home. In some embodiments, the delivery system is flat and comprises a folded structure. In one embodiment, the folded delivery system comprises a single fold (e.g., to panels connected by a hinged portion), such that, when folded, the assay tests are provided within the folded structure. The assay tests can be associated with the folded in structure in any manner. For example, in some embodiments, the assay tests (directly or contained within a protective encasement) are affixed to the inside of the folded structure by an adhesive. In other embodiments, the assay tests are enclosed in a pocket. In some preferred embodiments, the delivery system comprises two folds and three panels. An example of such a structure is shown in FIG. 19. In some preferred embodiments, the delivery system, when folded, has a length of 8.5 cm or less, a width of 5.5 cm or less, and a thickness of 1 mm or less. In preferred embodiments, the assay tests are provided on a portion of the folded structure such that opening of first flap exposes the assay test. The use of a three-panel delivery system provides six panel sides (i.e., each of the three panels has a front and back side). Delivery systems with multiple panels provide a surface area for the addition of text, figures, or attachment sites for additional materials. Such text, figures, and additional materials include, but are not limited to, branding, co-branding, instructions, information, or other attached materials (e.g., phone cards, etc. as described above).

In some preferred embodiments, the delivery system is manufactured to incorporate a desiccant so that environmental moisture does not affect the biosensors or otherwise impair the reaction means of the assay. In some embodiments, a desiccant material is placed in a chamber of the delivery system or attached to an interior surface of the container (e.g., lined in a plastic bottle or lined in a foil container). However, in preferred embodiments of the present invention, the desiccant material is incorporated into the material of the delivery system (e.g., the entire material, the walls, the bottom, the cap, etc.). In some embodiments, the inside of the container has a plug, liner, or sleeve that is made of an entrained desiccant that channels moisture away from the inside of the container and into the desiccant thereby keeping moisture away from the tests. In preferred embodiments the desiccant is co-molded at the same time as the container allowing the desiccant to form a sleeve within the container and channeling moisture away from the contents of the container. Methods for generating such desiccant-entrained polymers are described in U.S. Pat. Nos. 5,911,937 and 6,080,350, as well as PCT publications WO 98/39231, WO 99/63288, WO 99/62697, and WO 00/17259, each of which is incorporated herein by reference in their entireties. The presence of the desiccant in the material provides consistent drying capabilities throughout the container so that each of a plurality of tests contained in the container remain equivalently reliable over time. In some embodiments, the desiccant is not attached or associated with the delivery system (e.g., provided in an unattached pouch).

The present invention is not limited by the nature of the desiccant, or by the use of a desiccant. In some embodiments, the desiccant comprises one or more chemical compounds that form crystals that contain water (e.g., anhydrous salts), compounds that undergo a chemical reaction with water or moisture, and materials capable of moisture absorption through physical absorption (e.g., silica gels, molecular sieves, and naturally occurring clay compounds such as montmorillimite clay).

A number of container materials may be used in the generation of entrained desiccants. For example, matrix based polymers of the present invention can be basically any functionalized thermoplastic including anhydride or amine or acid or cyanate or isocyanate or hydroxy functionalized polymer. Examples of suitable matrix based polymers, as described in U.S. Pat. No. 6,080,350, include polypropylene maleic anhydride, polyethylene maleic anhydride, polystyrene maleic anhydride, polyethylene acrylic acid, polyethylene-urethere, polyethylene-EVOH and polyethylene-nylon. Other suitable thermoplastic materials include grafted polyolefins, polycarbonates, polyamides, ethylene-vinyl acetate partially hydrolyzed polymers, ethylene-methacrylate partially hydrolyzed polymer, grafted polyvinyl chloride, grafted polystyrene, polyester, polyester amide, polyacrylic partially hydrolyzed ester, acrylic, polyurethane and polyacetal or mixtures thereof. In some embodiments of the present invention, the desiccant containing material comprises channels to allow moisture to be eliminated by the entrained material. The channeling agent used in the present invention, as described in U.S. Pat. No. 6,080,350, can be generally any hydrophilic material. In one embodiment, the hydrophilic material is a polar compound having at least two hydroxy groups. Suitable channeling agents of the present invention include polyglycols such as polyethylene glycol and polypropylene glycol and mixtures thereof. Other suitable materials include EVOH, glycerin, pentaerithritol, PVOH, polyvinylpyrrollidine, vinylpyrollidone or N-methyl pyrollidone, with polysaccharide based compounds such as glucose, fructose, and their alcohols, and mannitol being suitable for the purposes of the present invention since they are hydrophilic compounds having numerous hydroxy groups.

The desiccant-containing delivery systems of the present invention are used to increase the shelf-life of the assay tests. Thus, when used in conjunction with the multiple-test-containing delivery systems of the present invention, the test can be accessed at different time periods and still maintain functionality (i.e., the ability to accurately detect the presence of alcohol in a sample). In some embodiments, tests may be stored and accessed for one month to two years or more and still maintain functionality (e.g., one month, two months, . . . one year, . . . two years, . . . ).

In some embodiments, no desiccant material is used at all. The present invention provides delivery systems and assay tests that allow the assay tests to remain functional over extended periods of time without desiccation. Test systems without desiccant are manufactured less expensively. Thus, the desiccant-free test systems of the present invention provide an advantage over available desiccant-containing systems.

In preferred embodiments, the delivery system acts as a storage container and stores multiple assay tests so that one or more assay tests can be accessed on a single occasion or on two or more distinct occasions. In some embodiments, the delivery system comprises a flat credit-card shaped structure (e.g., a folded structure as described above). In some embodiments of the present invention, the delivery system comprises a thin box, an oval, round, or other shaped cylinder, or other desired shapes, that includes one or more compartments for multiple assay test storage. In preferred embodiments, the storage container comprises a material such as hard plastic that protects the assay tests and increases their durability, while in other embodiments, the delivery system comprises a paper or cardboard-like material (e.g., laminated paper). In particularly preferred embodiments, the delivery system is constructed so that it can be easily opened to access assay tests. In other embodiments the delivery system is made of a hard plastic polymer with an entrained desiccant so that moisture is channeled away from the contents contained therein, maintaining a low humidity and preserving the viability of the reaction means of the assay tests. In other embodiments, removable protective encasements cover one or more compartments.

Storing multiple assay tests so that they can be accessed on a single occasion or two or more distinct occasions has several benefits. Multiple assay tests allow individuals to use more than one assay test on a given occasion, for example, to determine if their analyte concentration has increased or dropped over time. Additionally, because individuals may use assay tests on separate occasions, the delivery system stores a sufficient quantity of tests to last an individual a period of days, weeks, or months; thereby diminishing the need to continually replenish assay test supply. For example, where the tests are provided to consumers by a party other than the consumer, the distribution of the system by the secondary party is more efficient (e.g., requires less resources) if multiple tests are distributed at one time rather than providing tests on separate occasions. In addition, in some embodiments, it is desirable for the delivery system to be durable so that the assay tests are not damaged during distribution from a secondary party to a consumer (e.g., distribution by mail).

In some embodiments of the present invention, the delivery system is designed to allow easy access to the assay tests. For example, tests may be accessed by simply snapping open an air tight cap that covers one or more chambers containing the tests. In preferred embodiments the delivery system comprises a hard plastic polymer storage container with an entrained desiccant, thereby, protecting the assay tests inside from environmental moisture. In other embodiments, tests may be accessed by simply lifting a flap that covers one or more chambers containing the tests. Alternately, the tests may be directly accessed through an opening at one portion of a chamber. In yet other embodiments, the delivery system comprises a folded structure (e.g., two flaps connected by a hinge or three flaps connected by two hinges) whereby unfolding of the structure reveals one or more of the assay tests. In some of these embodiments, exposure of the assay tests to the environment is increased (a negative consequence) in trade for easier access (i.e., the assay tests are not completely sealed from exposure to moisture, air, light [e.g., ultra-violet light], heat fluctuations, and the like). In some embodiments, the assay tests comprise one or more stabilizers that increase shelf-life in response to environmental exposure.

In some embodiments of the present invention, assay tests are contained in a first package. The first package may contain one or more tests. In embodiments where the first package contains more than one test, the test may be contained in one or more compartments in the first package. In some embodiments, the first package is sealed to protect the assay tests from the environment. In some embodiments, one or more of the first packages are contained in a second package. In preferred embodiments, two or more first packages are contained in a second package which can be independently opened to gain access to the assay test. The present invention contemplates delivery systems comprising such first and second packages. In further embodiments, the delivery system provides placards so that instructions, labels, warnings, or other text or diagrams are easy to notice and read. In some embodiments, such materials are provided on the first or second packages or on the assay test itself.

In yet other embodiments, the delivery system stores multiple tests and is configured to dispense a single assay test without exposing the remaining tests to the environment. For example, in one embodiment, test strips are provided in a ribbon form within the delivery systems, wherein the tests are connected to one another end to end with a serration creating the division point between test strips. In some embodiments, the ribbon is provided in a roll within the delivery system. In such embodiments, a small portion of the end test strip can be exposed to the environment such that the reactive portion of said test strip is maintained within the delivery system without being exposed to light or moisture from the outside environment. A user pulls the end of the strip forward out of the device such that the reactive portion of the desired test strip and the end of the next test strip emerges from the delivery system. The serration between the desired test strip is then severed to release the desired test strip for use, leaving the end (the non-reactive end) of the next test strip exposed for future use. In still other embodiments, the multiple test strips are not connected to one another, but are still dispensed from the delivery system a single test strip at a time. In such embodiments, the user activates a selector contained on the delivery systems which forces a single test strip out of the delivery system while maintaining the remaining test strips within the protective environment of the delivery system (See e.g., U.S. Pat. No. 4,911,344, herein incorporated by reference in its entirety). In some embodiments, the test strip is dispensed by a pivoting cover having an internal finger portion that pushes the topmost test strip of a stack of test strips outwardly from the top of the dispenser as the cover pivots (See e.g., U.S. Pat. Nos. 4,171,753, 3,942,683, 3,845,882, 3,844,445, 3,565,284, 3,410,455, and 2,853,206).

B. Operation

In one preferred embodiment of the present invention, the delivery system is operated by opening the delivery system. In some embodiments, a test is then removed for use. In other embodiments, a removable protective encasement that covers a compartment of the delivery system is peeled or folded back or otherwise opened or removed to reveal an assay test. The assay test is then removed for use.

Figure 4:
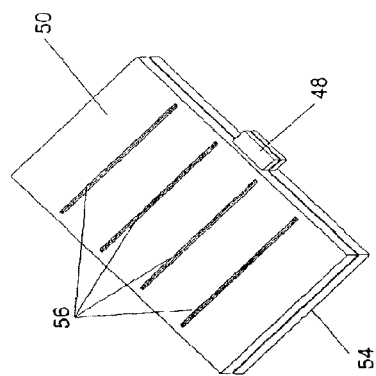
FIG. 4 shows a top view of the delivery system in FIG. 3 when closed.
Figure 3:
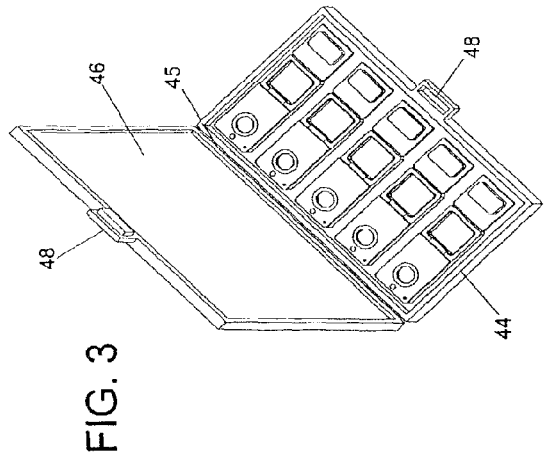
FIG. 3 shows a top view of a delivery system that stores multiple assay tests and is made with a hinge that allows the entire delivery system to be opened.
Figure 7:
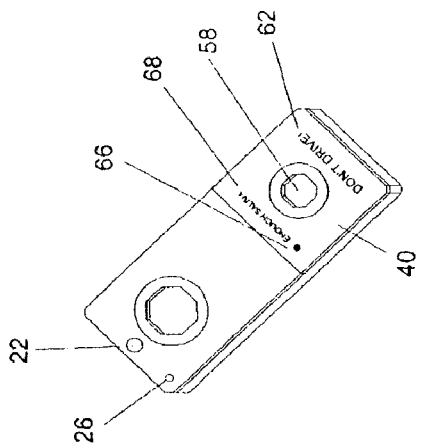
FIG. 7 shows a top view of an assay test from FIG. 1 where one end has been folded onto the other.

One embodiment of the delivery system of the present invention is illustrated in FIGS. 3 and 4. The delivery system is rectangular, flat, and thin, similar in size and shape to a credit card, so that it is easy to carry in a wallet, pocket, or purse. The delivery system is approximately 2 mm in thickness, and has overall dimensions of roughly 5.5 cm×8.25 cm, although smaller or larger delivery systems can be generated as desired. The components of the delivery systems in FIGS. 3 and 4 are a compartment 44, hinge 45, locking mechanism 48, indentations 56, and three placards 46, 50, and 54. The compartment 44 holds multiple assay tests and can hold fewer or more assay tests than are shown in FIG. 3. Assay tests are individually placed in a foil or other protective encasement 72, shown in FIG. 12a, so they can be used on separate occasions. In addition, multiple assay tests are individually placed in protective encasements 72 so that the supply of assay tests can last an individual a period of weeks or months. Further, multiple assay tests are contained in the delivery system so that individuals have enough assay tests to determine if their analyte concentration has dropped over time on one distinct occasion. Alternately, the compartment 44 can be covered with a removable protective encasement, which can be peeled back or otherwise removed to reveal an assay test as shown in FIG. 12b.

As shown in FIGS. 3 and 4, the hinge 45 is constructed in conjunction with the delivery system to form one molded part. The hinge 45 is made of a material such as plastic, although a variety of materials are contemplated by the present invention, that allows the delivery system to be easily opened and closed to access assay tests. The locking mechanism 48 is constructed so that the delivery system closes tightly to protect assay tests. In addition, the delivery system is constructed of a material such as hard plastic, although a variety of materials are contemplated by the present invention, that will protect the assay tests and add to their durability. The indentations 56 are molded to protrude into the compartment 44 to limit the ability of the assay tests to move and consequently become damaged while inside the delivery system. Finally, three placards 46, 50, and 54 allow instructions, labels, and warnings to be easily noticed and read. Placard 50 refers to the front of the top of the delivery system. Placard 46 refers to the back of the top of the delivery system. Placard 54 refers to the back of the bottom of the delivery system.

Figure 10:
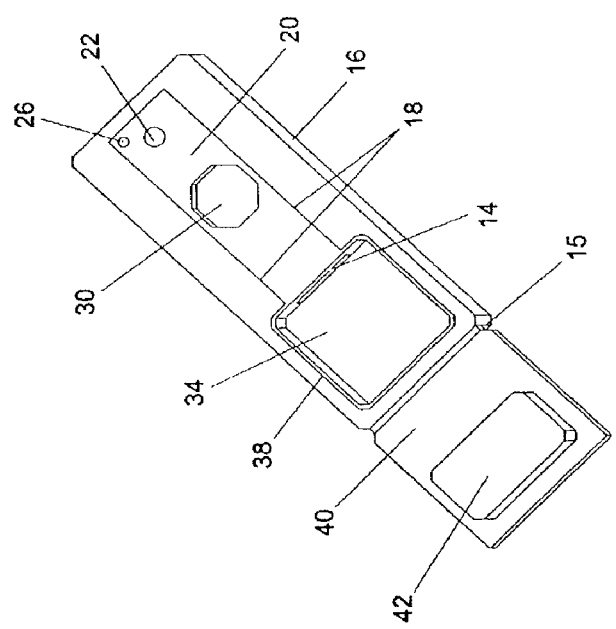
FIG. 10 shows an assay test similar to the assay test in FIG. 1 but constructed of two main components instead of three.
Figure 13B:
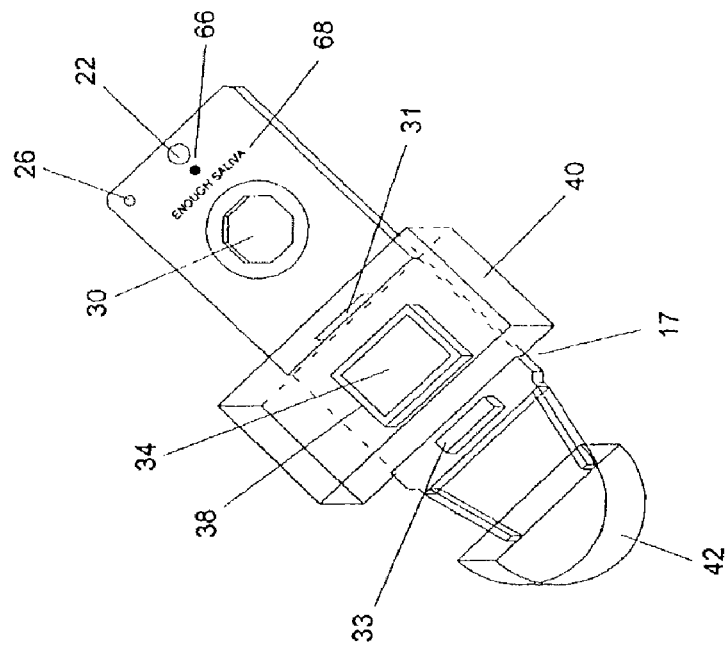
FIG. 13b shows an assay test similar to the assay test in FIG. 9, but which comprises a secondary chamber containing additional reaction components.
Figure 13A:
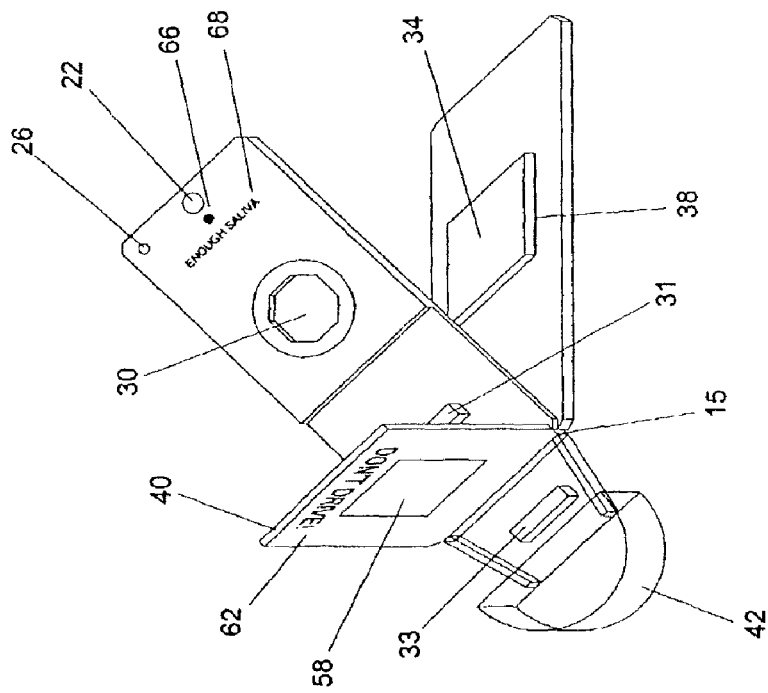
FIG. 13a shows an assay test similar to the assay test in FIG. 8, but which comprises a secondary chamber containing additional reaction components.
Figure 13F:
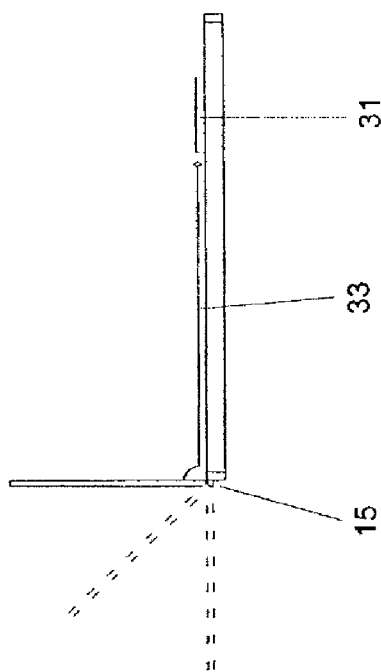
FIG. 13f shows a side view of the assay test in FIG. 13e.
Figure 13E:
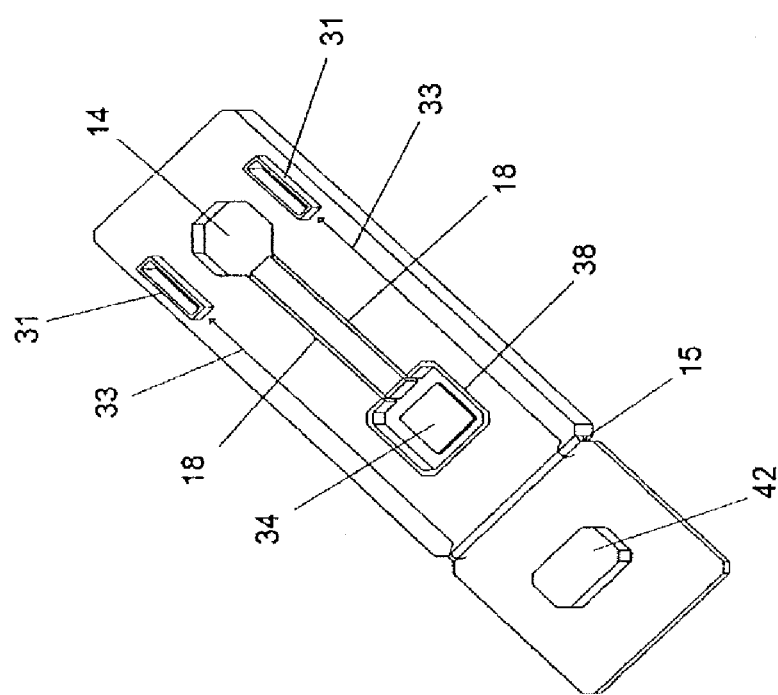
FIG. 13e shows the top view of an assay test similar to the assay test in FIG. 13c except that two chambers containing additional reaction components are located on the opposite end of the assay test from the chamber containing additional reaction components in FIG. 13c.

Additional embodiments of the assay tests are shown in FIGS. 8, 9, 10, and 13a-f. There are various possibilities to how the absorbent material 42 is fitted into the well 38 in one easy step. In FIG. 8, the hinge 15 allows both the well 38 and well covering 40 to easily fold, snap, and lock around the absorbent material 42. In FIG. 9, a sliding mechanism 17 replaces the hinge 15 so that the well 38 and well covering 40 easily slide on top of and tightly lock around the absorbent material 42. There are also various possibilities to the number of parts necessary to build an assay test. In FIG. 10, the top 21 is not used. Instead the middle 20 is colored such that the sheet 14 cannot be viewed except through the windows 30 and 22. In addition, there are various possibilities for the location of the reaction means. In FIGS. 13a-f, the reaction means is located on a sheet 14 and/or in one or more chambers 31. In FIGS. 13a-f, when an individual folds or slides the assay test to operate it, a protrusion 33 breaks open a chamber 31 and introduces the chamber's contents to the sheet 14, thereby releasing or mixing the components of the reaction means.

Figure 11:
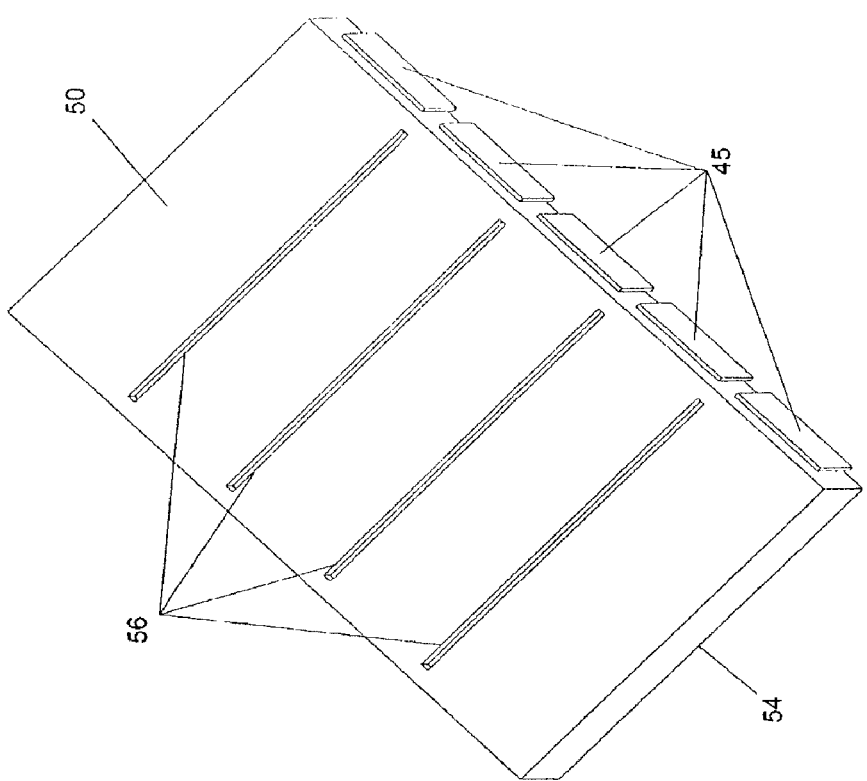
FIG. 11 shows a delivery system that stores multiple assay tests, and is made with five hinges that allow five compartments in the delivery system to be opened.

An additional embodiment of the delivery system is shown in FIG. 11. There are various possibilities to constructing a rectangular, flat, and thin delivery system that provides multiple placards and stores tests while making them easy to carry, easy to access on one or more occasions, and durable. In FIG. 11, there are five hinges 45. Each hinge 45 breaks off to reveal separate compartments containing assay tests.

From the description above, a number of advantages of the assay test systems of the present invention become evident. Because the assay test is contained within a single device, it is easy to use. For example, in some embodiments, the hinge on the assay test allows the test to be easily used in one step. In other embodiments, the assay test comprises a reaction means which relies on a chemical (e.g., enzymatic), biosensor, or other technology that provides the assay test with fast and accurate detection capabilities, lowers costs, and produces a controlled color or other detectable change. In some embodiments, the assay test has an indicator that ensures reliability by allowing the user to check if enough sample was put on the absorbent material. Also, in other embodiments, the large, easy to see window allows results to be easily read, and the pictorial and written instructions that appear on the assay test and/or delivery system allow results to be easily deciphered and interpreted.

Because the assay test and the delivery system are small and have relatively few parts, in some embodiments, the assay test and delivery system are inexpensive to manufacture. Because the delivery system comprises a rectangular, flat, and thin design, similar in size and shape to a credit card, in some embodiments, it is easy to carry in a wallet, pocket, or purse. Because the delivery system stores multiple assay tests that are protected by their own protective encasements, assay tests are easy to access individually on one or multiple occasions. In some embodiments, the hard material of which the delivery system is constructed protects the assay tests and adds to their durability. In yet other embodiments, the delivery system provides large placards that allow instructions, labels, and warnings to be easily noticed and read.

Figure 6:
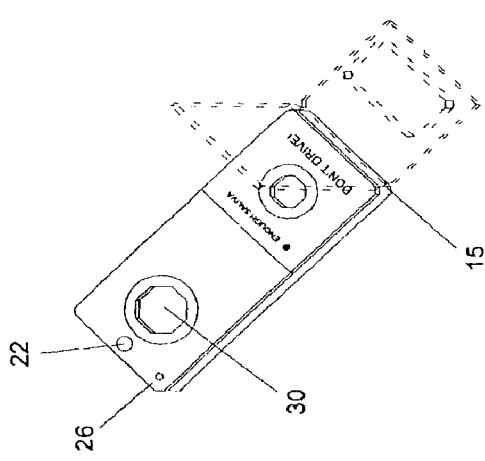
FIG. 6 shows how a hinge allows one end of an assay test from FIG. 1 to be folded onto another.
Figure 5:
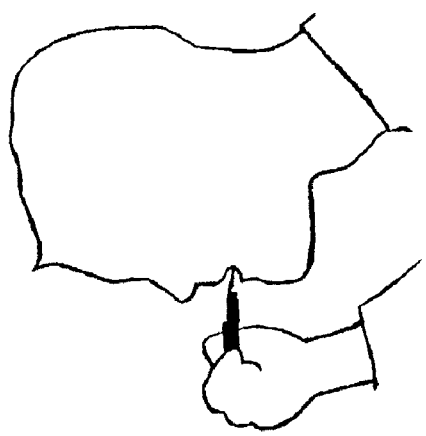
FIG. 5 shows an individual putting one end of an assay test from FIG. 1 into their mouth.

In some embodiments of the present invention, the delivery system operates by first unlocking the locking mechanism 48. Next, a user folds open the delivery system and removes one assay test enclosed in a protective encasement 72. The encasement 72 is then easily ripped open and an assay test is removed. As shown in FIG. 5, a user then saturates an absorbent material 42 on one end of the assay test with a saliva sample. Next, as shown in FIG. 6, the user, in one step, folds this saturated end into a well 38 on the opposite part of the test. The folding motion is quick and easy. Depending on the technology impregnated on the sheet 14, the user waits a short period of time. To check if enough saliva was initially put on the absorbent material 42, at the end of the waiting period, the user observes a color change or other detectable signal in the small circular window 22. The absence of a change in the window 22 indicates that enough saliva may not have been initially put on the absorbent material 42, and the assay test should not be used. Finally, the user checks if their saliva analyte concentration level is at or above a specific level by viewing a color change or other detectable signal in the large, easy to read, octagon shaped window 30. To make the assay test easy to decipher, the user compares the color changes or other detectable signals in the windows 22 and 30 to pictorial and written instructions printed on the test 58, 62, 66, and 68, and on the delivery system placards 46, 50, and 54.

In another embodiment of the present invention the delivery system comprises first and second packages. As shown in FIG. 14, a first package 102 contains an alcohol concentration test 105. In some embodiments, the first package comprises multiple compartments, each of which contain one or more alcohol concentration tests. The first package 102 comprises a first wall 103 and a second wall 104. The walls may be a single material or may comprises layers of different materials. In some embodiments, the walls comprise an inner layer (e.g., heat sealed plastic or polymer), an intermediate layer (e.g., a foil, polymer, or polymer film [SARAN, BARAX] layer), and an outer layer (e.g., a paper, cardboard, or polymer layer), while in other embodiments, four layer are provided including a tie layer (e.g., a plastic or polymer [polyethylene] layer) between the intermediate layer and outer layer. In some embodiments, the first package is sealed, preventing exposure of the assay test to the environment. A second package 99 comprises a first wall 100 and a second wall 101. The first and second walls are sealed along three sides. The open end provides an opening for the insertion or removal of one or more of the first packages 102 between the first wall 100 and second wall 101. In preferred embodiments, the second package is the approximate size and shape of a standard credit card. In some preferred embodiments, the first or second wall of the second package further comprises a thumb notch at the unsealed side to facilitate entry or removal of the first packages.

Figure 15:
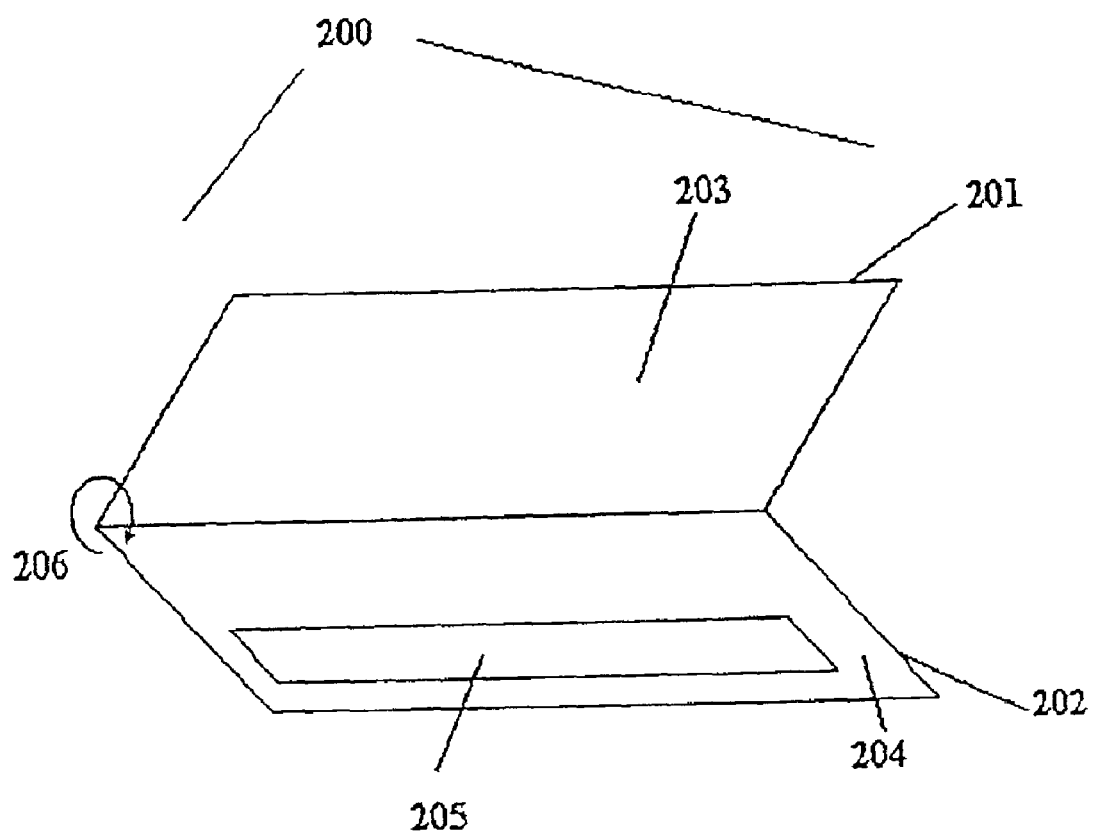
FIG. 15 shows one embodiment of the delivery systems of the present invention.

In another embodiment shown in FIG. 15, a first package 205 (as described above for first package 102) is enclosed in a second package 200. The second package 200 comprises a first wall 201 with an inner surface 203 and a second wall 202 with an inner surface 204. The first wall 201 and second wall 202 are connected along one edge by a hinge 206. The first package 205 is attached to the inner surface 204 of the second wall 202. When the hinge 206 is in the closed position, the first package 205 is enclosed within the second package 200. When the hinge 206 is in an open position, the first package 205 is accessible.

Figure 16:
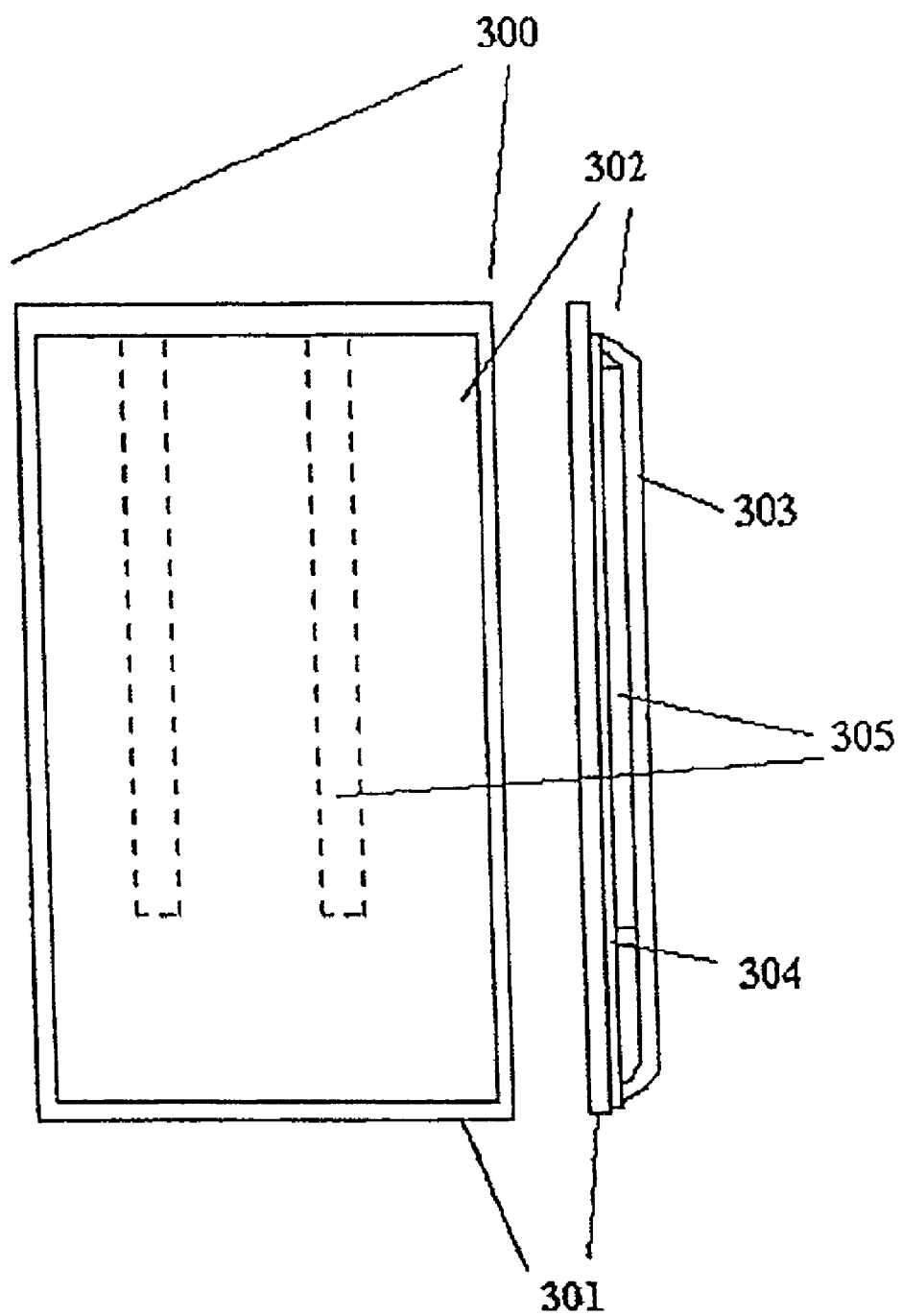
FIG. 16 shows one embodiment of the delivery systems of the present invention.

In another embodiment shown in FIG. 16 the delivery system 300 comprises a solid support 301 and an assay test 305 enclosed within a package 302. In some embodiments, the package 302 comprises multiple compartments, each of which contain one or more assay tests. The package comprises a first wall 303 and a second wall 304. The walls may be a single material or may comprises layers of different materials. In some embodiments, the walls comprise a heat sealed plastic inner layer, a foil intermediate layer, and a paper outer layer. In some embodiments, the first package is sealed, preventing exposure of the alcohol concentration test 305 to the environment. The second wall 304 of the package 302 is attached (e.g., glued) to the solid support 301. In preferred embodiments, the delivery system 300 is approximately the size and shape of a standard credit card.

In still other embodiments of the delivery system of the present invention, the delivery system is a rectangular, oval or round cylinder-like storage container, or other desired shape. In some embodiments, it is made of a hard plastic polymer, so that it is easy to carry in a pocket or purse. In particularly preferred embodiments, the storage container is approximately 2-3 mm in thickness, has a height of 5 cm or less and a diameter (e.g., outer diameter) of approximately 2.5 cm, although smaller or larger delivery systems can be generated as desired. An example of one such configuration is shown in FIG. 17. In this figures, the container comprises a cap that forms an airtight seal when snapped onto the container. In some embodiments, the cap is attached to the container by a hinge. In still further embodiments, the cap is sealed by a locking mechanism so that the delivery system closes tightly to protect assay tests and to provide an air tight seal to reduce the exposure of the tests to the outside environment. Such delivery systems find particular use with test assays that are in a test strip format. For example, as shown in FIG. 18, in some embodiments, the assay test strip is approximately 0.5 mm in thickness, and has overall dimensions of roughly 6.5 cm×5 mm, although both larger and smaller dimensions are contemplated and can be designed, as desired.

In yet other embodiments, the delivery system is provided as a folded structure, as exemplified in FIG. 19. In some preferred embodiments, the delivery system, when folded, has a length of 8.5 cm or less, a width of 5.5 cm or less, and a thickness of 1 mm or less. In this figure the folded structure has two folds and three panels, each panel having a front and back side. In some embodiments, the assay test is associated with a panel, such that it is exposed when the first flap is opened (e.g., the front of panel 1 or the back of panel 3 in FIG. 19). The remaining panels find use for displaying or providing attachment or insertion points for text, figures, or other desired materials (e.g., co-branding and phone cards), as described above. In preferred embodiments, the delivery system is FIG. 19 is composed of paper or cardboard stock (e.g., laminated paper or cardboard stock). In yet other preferred embodiments, the delivery system, when folded, is approximately the dimension of a credit card so as to facilitate its use in wallets or purses. While the folded delivery systems may not provide as much protection from the environment as sealed containers, in some embodiments, the folded delivery systems are inexpensive to produce, providing the appropriate combination of durability (e.g., using both folded delivery systems and attached foil packages that encase the assay tests to provide sufficient durability) and ease of use, cost efficiency, and the ability to provide substantial co-branding, instructions, and other desired materials (e.g., pre-paid phone cards, material for passing time, etc.).

Accordingly, it is clear that the assay test system of the present invention comprises assay tests and delivery systems that have many significant advantages. In some embodiments, the assay test is contained within a single device so that it is easy to use. In some embodiments, the assay test is also small, fast, accurate, inexpensive, and durable. In addition, in some embodiments, assay test results are easy to read and easy to decipher using either the delivery system or the assay test itself. The assay test relies on either a chemical, biosensor, or other detection technology as a reaction means. The delivery system stores multiple assay tests so that the assay tests can be easily accessed on one or more occasions. In some embodiments, the delivery system makes assay tests both easy to carry and durable. In other embodiments, the delivery system provides placards for instructions, warnings, and labels.

III. Analytes

The present invention provides detection assay tests for a wide variety of analytes. In preferred embodiments, the present invention provides oral assay tests for measuring analytes in saliva samples. The assay tests find use in the detection of analytes including, but not limited to, alcohol (e.g., for use by individuals in making decisions about whether or not to operate a motor vehicle), glucose (e.g., qualitative or quantitative tests for use by diabetics), ketones, cancer markers (e.g., prostate-specific antigen [PSA], epidermal growth factor receptor [EGFR], cancer antigen CA 15-3), illicit compounds (e.g., cocaine, cannabinoids [e.g., 11-carboxy-$\Delta^9$-tetrahydocannabinolic acid], opiates), caffeine, hormones (e.g., natural and synthetic hormones including aldosterone, testosterone, progesterone, andostenedione, estriol, estrone, steroids, fertility markers, pregnancy markers), antibodies, pathogens (e.g., *P. gingivalis*, *Chlamydia* organisms, *Streptococcus* organisms, etc.), growth factors (e.g., EGF, NGF, IGF-1), and other compound including, but not limited to, cortisol, serotonin, 5-hydoxytryptophane, methadone, phenytoin, primidone, carbamazepine, melatonin, insulin, DHEA sulfate, urea, uric acid, ammonia, cholesterol, lactoferrin, haliperidol, theophylline, cotinine, estradiol, salicyclic acid, acetaminophen, nitrazepam, clobazam, amphetamine, quinine, lithium, antibiotics (e.g., penicillin and tetracycline), vitamins, minerals (e.g., calcium), toxins, anti-oxidants, monosodium glutamate (MSG), components of food products (e.g., peanuts and/or tree nuts), proteins and nucleic acids (e.g., DNA and RNA), including host and non-host (e.g., pathogenic) proteins and nucleic acids.

Configurations of detection assays are illustrated below for several different classes of analytes. It will be appreciated that these configurations are applicable and adaptable to assay tests directed to the detection of other analytes.

A) Alcohol

Many of the costs, risks, and penalties associated with alcohol-related accidents could be prevented if individual alcohol consumers were capable of making a self-assessment of their capacity to engage in potentially dangerous activities. Although the inebriated individual often bears the greatest risk of harm from alcohol-related incidents, they may not have the motivation, knowledge, materials, or ability to take effective steps in preventing undesired alcohol-related incidents. The present invention provides systems that addresses the unmet need of providing individuals with easy to use and readily accessible alcohol concentration tests. The systems and methods of the present invention do not require the individual to incur substantial costs or expend substantial resources in obtaining and using the alcohol concentration tests—greatly increasing the likelihood that the tests are used and the associated benefits incurred.

In preferred embodiments, the assay tests are portable and durable and can be carried and stored in a wallet or purse. The consumer may use the test at home as a method of learning how to gauge physical symptoms associated with particular blood alcohol concentrations. The alcohol consumer may also read instructional and educational materials that accompany the test, gaining a better understanding of the relationship between alcohol impairment and accidents. In preferred embodiments, the test is used following alcohol consumption as a method for aiding the determination of fitness to drive. If the test indicates blood alcohol concentration (BAC) levels associated with risk of driving, the consumer chooses not to drive, reducing the risk of accidents. In some embodiments, a group of alcohol consumers are each tested to determine the most suitable driver or drivers within the group. In other embodiments, an alcohol consumer, upon receiving a result indicating impairment, waits for a time period and conducts subsequent testing until the results suggest fitness to operate a motor vehicle. In some embodiments, the assay tests are provided with time-consuming materials to help occupy the consumers' time between testing events. In other embodiments, information (e.g., taxi information) is provided to assist the consumer in selecting a safe course of action if the test indicates a lack of fitness.

In some embodiments of the present invention, alcohol providers such as bars, restaurants, and alcohol manufacturers and distributors provide alcohol concentration tests to consumers. For example, in some embodiments, a restaurant may implement a wait-and-retest program (e.g., providing multiple tests and educational information and/or incentives such as free non-alcoholic beverages until a suitable test result is obtained).

In preferred embodiments, the alcohol concentration assays tests are stable in the for at least one month, preferably for at least six months, more preferably for at least one year, and most preferably for at least two years. For example, in some embodiments, the assay test is temperature stable and possesses a long shelf life (e.g., maintains function for over a year at room temperature and for over three months at 104° F.).

A wide variety of reaction means are compatible with the present invention. In preferred embodiments, acceptable reaction means are those that can be incorporated into the assay tests of the present invention and that can generate and maintain a detectable signal in the presence of alcohol (e.g., methanol, ethanol, etc.). In some embodiments, the reaction means is selected and tailored to achieve desired reaction speed, accuracy, reliability, cost, and durability. For example, a variety of chemical reactions that provide colorimetric detection of ethanol in a sample are described in U.S. Pat. Nos. 5,032,506, 4,629,697, 4,642,286, 5,290,683, 5,589,349, 5,429,932, 5,429,931, 5,416,004, 4,786,596, 4,810,633, 4,734,360, 5,525,481, 5,141,854, 5,403,749, incorporated herein by reference in their entireties.

In preferred embodiments, the chemicals used at the reaction site are non-toxic, non-irritant and/or are not carcinogenic. This presents a problem because many chromogens cause toxic reactions, irritation or are carcinogenic if used orally. In contrast, the present invention provides chemistries that are non-toxic, non-irritant and/or non-carcinogenic. Indeed, any non-toxic, non-irritant and/or non-carcinogenic chromogen finds use with the present invention. A chromogen with unknown toxicity can be tested for toxicity by exposing several doses of the material to a test subject (e.g., an animal or human) and detecting undesired toxic responses. If no undesired toxic responses are observed when the chromogen is used at a functional (e.g., colorimetric) concentration, when exposed to the subject in a manner consistent with the methods of the present invention (e.g., placed in the mouth of a subject on a colorimetric test strip), then the candidate compound may be designated non-toxic and incorporated into the test assays of the present invention. The protocol in Example 1 may be followed to determine whether or not a candidate material for use in the reaction site of the test assay is toxic/non-toxic or an irritant/non-irritant. To avoid carcinogenicity, components of the reaction means are selected such that they are known not to have carcinogenicity (See e.g., CRC Handbook of Identified Carcinogens and Noncarcinogens). For compounds where the carcinogenicity is unknown, testing can be conducted to determine whether the candidate compound is, or is not, a carcinogen using any technique known in the art.

In some embodiments, the present invention provides potassium iodide (KI) as a chromogen. Assay tests containing potassium iodide were tested as non-toxic and non-irritant using the protocol in Example 1. Potassium iodide is an approved food additive whose use at 0.01% in iodized salt is well recognized. The amount of potassium iodide used in an assay test (e.g., 133 micrograms) is equivalent to the amount contained in 1-2 grams of iodized salt, and presents no safety concerns. Potassium iodide was found to provide a stable, detectable, colorimetric chromogen for use in the assay tests of the present invention. Potassium iodide also provides a chromogen suitable for use in on/off type assay readouts. Embodiments employing non-toxic chromogens are described in detail below.

In preferred embodiments, the reaction site of the present invention provides an on/off readout if the alcohol concentration level of the sample is above a certain threshold concentration. For example, an assay test designed to detect a sample concentration equivalent to a blood alcohol concentration of 0.04% would not change color at concentration significantly under 0.04% (off), but would change color at concentrations at or above 0.04% (on). The on/off format can be accomplished, for example, by the addition of competitive inhibitors or scavengers that prevent the colorimetric reaction unless the threshold concentration is reached, whereupon the competitor or scavenger is swamped out and the substrate is available to initiate the colorimetric reaction. Embodiments employing on/off reactions are described in detail in the example section below. In yet other embodiments, the detection readout is a gradient readout, wherein the color change gradually increases in intensity with an increase in alcohol concentration. In some embodiments, both on/off and gradient detections readouts are combined in a single assay. In some embodiments of the present invention, multiple collection sites and reaction sites are used. The plurality of collections sites find use, for example, in detecting different threshold concentrations of alcohol (e.g., a first collection site that detects 0.4% and a second collection site that detects 0.8%), different detectable readouts (e.g., different colors or a first collection site that shows a color and a second collection site that produces a symbol, shape, or word), different read-out formats (e.g., a first collection site that uses an on/off readout and a second collection site that uses a gradient readout), different detection purposes (e.g., detection versus indicator or detection of different analytes) and the like.

In some preferred embodiments, stabilizers are used to make the assay test durable. For example, in some embodiments of the present invention, the assay tests of the present invention remain functional for over a year when maintained at room temperature and for over three months at 104° F. This durability is enhanced when the assay tests are stored in the delivery systems of the present invention. For example, in some embodiments, assay tests enclosed in a delivery system remain functional for over two years.

Certain illustrative chemistries for use at the reaction site are provides below. The exemplary chemistries are not intended to limit the scope of the invention. In one embodiment of the present invention, the chemicals used at the reaction site are prepared in several submixes prior to combination and application on the desired solid support (e.g., test strip). The first submix comprises water (RO/DI water) (0.48 kg), dextran (40.0 g), starch (7.50 g), and gelatin (6.25 g). The water is added to a suitably sized vessel, followed by addition, with stirring, of dextran, starch, and gelatin. The components are stirred until homogenous (of even appearance). The solution will be milky in appearance. After the solution is homogenous, the mixture is heated to boiling (100° C.) for three minutes after the mix turns clear. The mixture is then cooled with stirring (ice should not be used). The mixture may become slightly cloudy after cooling.

The second submix comprises water (RO/DI water) (240 g), potassium EDTA (120 mg), citric acid (11.53 g), and potassium iodide (12.5 g), L-Cysteine, and sodium nitrite (the amounts of L-Cysteine and sodium nitrite are dependent on the activity of the alcohol oxidase). L-Cysteine and sodium nitrite may be used at 290 mg/L and 130 mg/L respectively. However, to achieve maximal results, multiple concentrations should be made that are, for example, 10% higher and lower in concentration of L-Cysteine and sodium nitrite, where each concentration is tested against the specific enzyme lot to be used to determine the best concentration for use with the particular enzyme lot. A desired concentration provides an accurate, reliable, and detectable readout. For example, a desired concentration provides minimal false negative and false positives. In preferred embodiments, where the test is to detected an alcohol concentration of 0.04%, there are not false positives when a 0.000 control is used, no more than 15% false positives when 0.016 is used, and no more than 0.01% false negative results when 0.064 is used. The water is added to a suitably sized vessel, followed by addition, with stirring, of the potassium EDTA, L-Cysteine, and citric acid until completely dissolved. The pH of the mixture is adjusted to approximately 6.4 (e.g., using sodium hydroxide and HCl as necessary). Once the pH is adjusted, sodium nitrite and potassium iodide are added and the mixture is stirred until everything is dissolved. The solution should be clear in color.

The third submix comprises water (RO/DI water) (20 g), sodium phosphate, dibasic, heptahydrate (134 mg), alcohol oxidase (80 KU), peroxidase (48 KU), catalase (45 KU), and STABILGUARD (130 ml) (SurModics, Inc., Eden Prairie, Minn.). The water is added to a suitably sized vessel, followed by addition, with stirring, of the sodium phosphate dibasic, heptahydrate. The pH of the solution is adjusted to approximately 7.0. While gently stirring the phosphate buffer solution, the peroxidase is added and slowly stirred until it is dissolved (approximately 10 minutes). This solution is the peroxidase mixture. In a separate vessel, the alcohol oxidase is added and slowly stirred while the peroxidase mixture is added. Next, the catalase and STABILGUARD are added. The mixture is gently stirred for approximately 30 minutes. The solution should be a clear, cherry color.

In a vessel large enough to hold all three submixes, the submixed are added together and stirred until completely mixed. Lactitol (50 g) is added and thoroughly mixed until dissolved. The solution should be yellow and slightly cloudy. The solution is then mixed gently at room temperature for 90 minutes as an incubation period. The solution should be used within 6 hours of preparation. To use, the solution is applied to a desired test assay (e.g., applied to an absorptive material on a test strip). For example, the reaction mixture may be applied to a thin strip of filter paper and dried (160° F.) to create a test strip. Application and drying are preferably conducted in a low humidity environment (e.g., ambient humidity of less than 5%, preferably less than 3%, and most preferably less than 2%) to facilitate fast drying and maintain optimal reactivity and performance of the assay tests. In some preferred embodiments, all manufacturing steps are carried out in a low humidity environment. In some embodiments, formulations are made as above, but without catalase, nitrite, or citrate.

Each of the components present on the test strip are non-toxic and non-carcinogenic. Each are found as food ingredients, approved food additives or substances normally encountered in the diet or produced normally in the body. Amounts present in the testing pad (e.g., 133 micrograms of potassium iodide, 0.2 micrograms of sodium nitrite, 1.3 micrograms of EDTA, sodium salt, 4.7 micrograms of cysteine, 123 micrograms of citric acid, 533 micrograms lactitol, and 0.6 micrograms disodium phosphate), only a portion of which would be solubilized and ingested, represent small fractions of the amounts encountered in the daily diet and from other sources such as in pharmaceutical products.

This reaction site provides a stable, accurate, inexpensive, non-toxic, non-irritant, non-carcinogenic on/off chemistry for use in alcohol detection. The reaction time is less than two minutes and remains positive for at least twenty additional minutes.

B) Glucose

The present invention provides non-invasive glucose tests. For example, the present invention provides oral glucose tests for monitoring glucose levels from saliva. The glucose levels in saliva correlate with blood glucose levels and can be used, whether quantitative or qualitative, in the management of diabetes. Currently four billion dollars a year is spent on glucose testing for diabetics throughout the world. It is estimated that there are 16 million diabetics in the United States and many more throughout the world. However, only 8 million of the diabetics in the United States have been diagnosed with the disease. Approximately 7 million of these diagnosed individuals are Type 2 diabetes and 1 million are Type 1 diabetes. Type 1 diabetics must constantly measure and manage their glucose levels and must take insulin. Failure to correctly manage glucose levels in both Type 1 and Type 2 diabetics could result in death. However, such negative consequences are more likely and occur faster in Type 1 diabetics.

Current accurate products for measuring glucose levels involved taking a blood sample (e.g., pricking a finger) and having blood glucose measured using a portable electronic meter. Other expensive but accurate and non-invasive products are being developed largely for Type 1 diabetics including techniques such as infra-red scanning. Less accurate urine tests are available for Type 2 diabetics. Because of the nature of current diagnostics, Type 2 diabetics do not test themselves very often. Hence, there is a market need for Type 2 diabetics to test themselves with an inexpensive, qualitative, non-invasive product. The assay tests of the present invention meet these needs.

In some embodiments of the present invention, the glucose test assay is a qualitative assay, indicating the presence of glucose at or above a particular threshold level. Qualitative assays find use by diabetics in monitoring glucose levels, wherein the information is used in making dietary and/or medical decisions. In other embodiments, the glucose test assay is a quantitative assay, wherein a particular concentration of glucose is determined.

Glucose assay tests of the present invention may be used with the delivery systems of the present invention, provide durability, improved shelf-life, and ease-of-use.

The non-toxic, non-irritant, non-carcinogenic reactions means discussed above for alcohol detection finds use in the glucose assay tests. Glucose oxidase is supplied in place of alcohol oxidase. Glucose oxidase reacts with glucose present in the saliva sample to generate gluconic acid and hydrogen peroxide. The hydrogen peroxide, like that in the alcohol detection assay, stimulates a color response. Thus, in some preferred embodiments, the present invention provides a glucose assay test comprising glucose oxidase and a non-toxic chromogen (e.g., potassium iodide). In other embodiments, the reaction means comprises hexokinase which reacts with glucose to form glucose-6-phosphate with the concomitant conversion of $NADP^+$ to NADPH. The $NADP^+$/NADPH conversion may be coupled to a color detection system (See e.g., U.S. Pat. Nos. 5,032,506 and 5,036,000, herein incorporated by reference in their entireties). In preferred embodiments, the reaction means containing the oxidase and chromogen is present in a reactive pad on the end of a test strip, wherein the pad is placed directly in the mouth. Additional systems, chemistries, and detection modes for carrying out glucose detection are described in U.S. Pat. Nos. 6,102,872, 3,964,871, 5,217,691, 5,140,985, 6,194,224, 5,179,288, 5,714,341, 5,989,917, 4,476,222, and 5,912,139, herein incorporated by reference in their entireties.

C) Other Assay Tests

1) Prostate-Specific Antigen (PSA)

The present invention provides non-invasive, inexpensive PSA tests. For example, the present invention provides oral PSA tests for monitoring PSA levels from saliva. High PSA levels in saliva correlate with prostate cancer, a noncancerous (benign) enlargement of the prostate (benign prostatic hypertrophy), and infected or injured (trauma) prostate. Every male over the age of 50 in the world should be tested regularly for prostate cancer. Current methods for testing for prostate cancer are two-fold: either an invasive rectal exam or expensive blood work. Because tests are invasive and expensive, many people are not tested regularly, or at all.

In some embodiments of the present invention the reaction means of the assay tests of the present invention contains an anti-PSA antibody (i.e., any immunoglobulin molecule that specifically interacts with PSA or a unique epitope of PSA). The reaction site is placed into the mouth to allow binding free PSA in the saliva to the anti-PSA antibody. The bound complex is then detected using any system of method known in the art. In some embodiments, detection requires the use of a detection apparatus. Systems and methods for PSA detection are described in U.S. Pat. Nos. 5,614,372 and 6,200,765, herein incorporated by reference in their entireties.

2) Ketones

The present invention provides non-invasive, inexpensive ketone tests (i.e., detection of ketone bodies such as acetone, acetoacetic acid and β-hydroxybutyric acid). For example, the present invention provides oral ketone tests for monitoring ketone levels in saliva. Approximately 2.5 million people world-wide are performing diets where ketone levels should be monitored. Also, there are approximately 1-5 million high performance athletes that should regularly measure ketone levels. If dieters' or athletes' ketone levels increase too high, they can go into acidosis and their bodies process muscle tissue instead of fat. The qualitative and/or quantitative measurement of ketone concentrations is important because of the relationship between elevated serum ketone levels and clinical conditions such as diabetes, disorders of the digestive organs, renal insufficiency, uremia and malignant carcinoma. In the course of these disorders, ketone bodies pass into the blood stream and a state of metabolic acidosis (ketosis) occurs. Monitoring for the onset of ketosis is of particular importance in the maintenance of diabetics because the occurrence of ketosis may indicate the need for modification of insulin dosage or other disease management.

The non-toxic, non-irritant, non-carcinogenic reactions means discussed above for alcohol and glucose detection finds use in the ketone assay tests. In some embodiments, the ketone is reacted with enzymes to form oxidized or reduced products (e.g., hydrogen peroxide, $NADP^+$ or NADPH) that can be detected in the systems described above. For example, in some embodiments, the reaction means comprises a dehydrogenase (e.g., 3-hydrocybutric dehydrogenase) which causes $NADP^+$/NADPH conversion (See e.g., U.S. Pat. No. 5,618,686, herein incorporated by reference in its entirety). The $NADP^+$/NADPH conversion may be coupled to a color detection system (See e.g., U.S. Pat. Nos. 5,032,506 and 5,036,000, herein incorporated by reference in their entireties). Additional systems, chemistries, and detection modes for carrying out ketone body detection are described in U.S. Pat. Nos. 3,880,590, 4,440,724, 4,405,721, 4,184,850, 4,097,240, 3,212,855, 4,970,172, and 4,147,514, herein incorporated by reference in their entireties.

Because glucose and ketone levels are both relevant to diabetics, in some embodiments, the present invention provides assay tests that simultaneously detect glucose and ketone levels.

3) Cortisol

The present invention provides non-invasive, inexpensive cortisol tests. For example, the present invention provides oral cortisol tests for monitoring cortisol levels in saliva. Cortisol is a hormone that has specific correlation to mood management and behavior. Low cortisol levels likely result in a person being in a bad mood and also may have an impact on blood pressure. Currently 1.5 million cortisol tests are performed each year.

In some embodiments of the present invention the reaction means of the assay tests of the present invention contains an anti-cortisol antibody (i.e., any immunoglobulin molecule that specifically interacts with cortisol or a unique epitope of cortisol). The reaction site is placed into the mouth to allow binding free cortisol in the saliva to the anti-cortisol antibody. The bound complex is then detected using any system of method known in the art. In some embodiments, detection requires the use of a detection apparatus. Systems and methods for cortisol detection are described in U.S. Pat. Nos. 5,910,575, and 4,311,690, herein incorporated by reference in their entireties.

EXAMPLE 1

Toxicity/Irritation Test

Ten healthy male Golden Syrian Hamsters are assigned to two groups of five animals/group. Group 1 is dosed with aliquots of solution containing the detection assay component at a concentration equivalent that intended for use in the detection assay, as well as, one or more diluted or concentrated samples (e.g., 2, 5, 10, and 100-fold dilute and concentrated compared to the intended use concentration) and Group 2 is dosed with saline. Prior to study initiation, the left cheek pouch of all animals is abraded using emery paper (everted and three areas of the mucosa abraded with three firm strokes of fine grit emery paper). Only animals with scalar notations of "zero" for erythema and edema for both left and right pouches are used. Following site preparation, 0.1 ml of the test or placebo is gently applied to the buccal mucosa of the left and right cheek pouch using a 1 cc tuberculin syringe. This procedure is repeated twice daily for four consecutive days and once on the fifth consecutive day. Prior to the first and each subsequent treatment, food particles are cleared from the left and right cheek pouches with approximately 20 ml of distilled water (room temperature) using a syringe equipped with a 12 gauge, 2 inch long blunt needle covered with rubber tubing. The left and right pouch are everted and examined for cleanliness. If food particles remain, the rise is repeated. The clean everted pouch is examined and scored with the aid of an incandescent high intensity light.

Erythema and edema are scored prior to each treatment and prior to necropsy in the left and right pouch of each animal. The animals are observed once daily for mortality, toxicity and pharmacologic effects. Body weights are recorded pretest and at termination. Following the last observation of day 5, the animals are humanely sacrificed and the left and right pouches are preserved in 10% neutral buffered formalin for histopathologic evaluation. The Group Average Mucosal Irritation Scores are calculated for both intact and abraded pouches.

The following scoring scale is used:

|  | VALUE |
|---|---|
| ERYTHEMA & ESCHAR FORMATION | |
| Natural pink condition of mucosa | 0 |
| Well-defined erythema | 1 |
| Moderate to severe erythema | 2 |
| Severe erythema (beet redness) | 3 |
| Loss of color (blanching of mucosal, etc.) | 4 |
| EDEMA FORMATION | |
| Normal condition (note folds in mucosa) | 0 |
| Slight edema | 1 |
| (edges of area well-defined by definite raising) | |
| Moderate edema (area raised approximately 1 mm) | 2 |
| Severe edema | 3 |
| (raised >1 mm & extending beyond exposure area) | |
| Blistering | 4 |

For each group at each time period, the individual erythema scores are added and the sum divided by the number of scores added to obtain the Group Average Erythema Score for each time period for the intact and abraded sites. This procedure is repeated using the edema scores to obtain the Group Average Edema Scope for each site at each time period.

For each day, the group average erythema scores for each time period and the group average edema scores for each time period are added and this sum divided by four (4) to obtain the Daily Group Average Mucosal Irritation Score.

In some embodiments, only materials that have an average score of less than two for each of the erythema and edema scores are used in detection assays. Preferably, the average score is less than 1 (i.e., non-toxic, non-irritant). In particularly preferred embodiments, the average score is less than 0.8 or even more preferably, less than 0.5. Any other suitable testing procedure may also be used (See e.g., Toxicology Testing Handbook: Principles, Applications, and Data Interpretation, ed. Jacobson-Kram and Keller, 2001).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. A method for detecting the presence of alcohol in saliva, comprising:
   a) contacting an assay test comprising a reaction site comprising i) a chromagen, wherein said chromagen is potassium iodide, ii) an alcohol oxidase enzyme, and iii) a peroxidase enzyme with saliva from a subject under conditions such that said saliva contacts said reaction site; and
   b) detecting the presence or absence of a visibly detectable signal in said reaction site, wherein said visibly detectable signal comprises a color change that occurs at a saliva alcohol concentration at or above a threshold level and wherein no color change occurs below said threshold level.

2. The method of claim 1, wherein said threshold level is equivalent to a blood alcohol concentration of 0.04%.

3. The method of claim 1, said assay test comprises a test strip.

4. The method of claim 3, wherein said test strip comprises an absorbent material, wherein said reaction site is located within said absorbent material.

5. The method of claim 1, wherein said color change is detectable by the human eye.

* * * * *